US012275778B2

(12) United States Patent
Kroner et al.

(10) Patent No.: US 12,275,778 B2
(45) Date of Patent: Apr. 15, 2025

(54) ANTI-TROPONIN T ANTIBODIES

(71) Applicant: Roche Diagnostics Operations, Inc., Indianapolis, IN (US)

(72) Inventors: Frank Kroner, Geretsried-Gelting (DE); Michael Schraeml, Penzberg (DE); Sarah Liedke, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1091 days.

(21) Appl. No.: 17/015,662

(22) Filed: Sep. 9, 2020

(65) Prior Publication Data

US 2021/0009668 A1 Jan. 14, 2021

Related U.S. Application Data

(63) Continuation of application No. PCT/EP2019/056069, filed on Mar. 12, 2019.

(30) Foreign Application Priority Data

Mar. 14, 2018 (EP) .................................. 18161697

(51) Int. Cl.
*C07K 16/18* (2006.01)
*G01N 33/53* (2006.01)
*G01N 33/68* (2006.01)

(52) U.S. Cl.
CPC ......... *C07K 16/18* (2013.01); *G01N 33/6887* (2013.01); *C07K 2317/565* (2013.01); *C07K 2317/567* (2013.01); *C07K 2317/92* (2013.01); *C07K 2317/94* (2013.01); *G01N 2333/4712* (2013.01); *G01N 2800/325* (2013.01)

(58) Field of Classification Search
CPC .............. C07K 16/18; C07K 2317/565; C07K 2317/567; C07K 2317/92; C07K 2317/94; G01N 33/6887; G01N 2333/4712; G01N 2800/325; G01N 33/53; G01N 33/6854
See application file for complete search history.

(56) References Cited

U.S. PATENT DOCUMENTS

| | | | |
|---|---|---|---|
| 5,316,757 A | 5/1994 | Sherry et al. |
| 5,342,606 A | 8/1994 | Sherry et al. |
| 5,385,893 A | 1/1995 | Kiefer |
| 5,403,482 A | 4/1995 | Steere et al. |
| 5,428,139 A | 6/1995 | Kiefer et al. |
| 5,428,155 A | 6/1995 | Sherry et al. |
| 5,462,725 A | 10/1995 | Kiefer et al. |
| 5,480,990 A | 1/1996 | Kiefer et al. |
| 5,739,294 A | 4/1998 | Kiefer et al. |
| 5,750,660 A | 5/1998 | Kiefer et al. |
| 5,834,456 A | 11/1998 | Kiefer et al. |
| 5,877,397 A | 3/1999 | Lonberg et al. |
| 5,885,793 A | 3/1999 | Griffiths et al. |
| 5,969,108 A | 10/1999 | McCafferty et al. |
| 6,333,397 B1 * | 12/2001 | Katus .................. G01N 33/6887 435/7.1 |
| 6,376,206 B1 | 4/2002 | Katus et al. |
| 2010/0111856 A1 | 5/2010 | Gill et al. |

FOREIGN PATENT DOCUMENTS

| | | |
|---|---|---|
| CN | 102565422 B | 7/2012 |
| CN | 106124771 A | 11/2016 |
| EP | 0394819 A2 | 10/1990 |
| JP | H037597 A | 1/1991 |
| JP | H11505605 A | 5/1999 |
| JP | 2010527920 A | 8/2010 |
| JP | 2012518418 A | 8/2012 |
| JP | 2013513108 A | 4/2013 |
| WO | 1994020627 A1 | 9/1994 |
| WO | 9633415 A1 | 10/1996 |
| WO | 2008141049 A1 | 11/2008 |
| WO | 2010099079 A1 | 9/2010 |
| WO | 2011068680 A1 | 6/2011 |
| WO | 2012107419 A1 | 8/2012 |

OTHER PUBLICATIONS

Almagro JC, Daniels-Wells TR, Perez-Tapia SM, Penichet ML. Progress and Challenges in the Design and Clinical Development of Antibodies for Cancer Therapy. Front Immunol. Jan. 4, 2018;8:1751. doi: 10.3389/fimmu.2017.01751. PMID: 29379493; PMCID: PMC5770808. (Year: 2018).*

Winkler K. Changing the antigen binding specificity by single point mutations of an anti-p24 (HIV-1) antibody. J Immunol. Oct. 15, 2000;165(8):4505-14. doi: 10.4049/jimmunol.165.8.4505. PMID: 11035090. (Year: 2000).*

Herold EM, John C, Weber B, Kremser S, Eras J, Berner C, Deubler S, Zacharias M, Buchner J. Determinants of the assembly and function of antibody variable domains. Sci Rep. Sep. 25, 2017;7(1):12276. doi: 10.1038/s41598-017-12519-9. PMID: 28947772; PMCID: PMC5613017. (Year: 2017).*

E.-C. Brockmann et al. Synthetic single-framework antibody library integrated with rapid affinity maturation by VL shuffling, Protein Engineering, Design and Selection, vol. 24, No. 9, Jun. 16, 2011, pp. 691-700.

Holger E. Thie, "Affinity maturation by random mutagenesis and phage display", Antibody Engineering vol. 1, Jan. 1, 2010, pp. 397-409.

"In vitro affinity maturation of recombinant antibodies by combination of pre-selected CDR-library pools", ip.com Journal, Oct. 16, 2007, pp. 1-7.

(Continued)

*Primary Examiner* — Hong Sang
*Assistant Examiner* — Carol Ann Chase
(74) *Attorney, Agent, or Firm* — Taft Stettinius & Hollister LLP

(57) ABSTRACT

The present invention relates to improved variant monoclonal antibodies binding to cardiac troponin T and having a better $K_D$ than the monoclonal antibody 12.1A11.11-7, produced by hybridoma clone 7.1 A 12.2-22 (ECACC 89060901) as deposited with European Collection of Animal Cell Cultures, GB.

10 Claims, 5 Drawing Sheets

Specification includes a Sequence Listing.

(56) References Cited

OTHER PUBLICATIONS

Juan C. Almagro et al., "Antibody engineering: Humanization, affinity maturation, and selection techniques," Therapeutic Monoclonal Antibodies: From Bench to Clinic, Oct. 1, 2009, pp. 311-330.

Kim Hyung-Yong et al., "Affinity Maturation of Monoclonal Antibodies by Multi-Site-Directed Mutagenesis," Monoclonal Antibodies: Methods and Protocols, Jan. 1, 2014 pp. 407-420.

Margit Mueller-Bardorff et al., "Improved troponin T ELISA specific for cardiac troponin T isoform: assay development and analytical and clinical validation," Clinical Chemistry, vol. 43, No. 3, Jan. 1, 1997, pp. 458-466.

Renaut Laurence et al., "Affinity maturation of antibodies: optimized methods to generate high-qualify ScFv libraries and isolate IgG candidates by high-throughput screening," Methods in Molecular Bio., vol. 24, Jan. 1, 2007, pp. 301-317.

Wark K L et al., "Latest technologies for the enhancement of antibody affinity," Advanced Drug Delivery Reviews, vol. 58, No. 5-6, Aug. 7, 2006, pp. 657-670.

Altschul, Stephen F. et al., Gapped BLAST and PSI-BLAST: a new generation of protein database search programs, Nucleic Acids Research, 1997, pp. 3389-3402, vol. 25, No. 17.

Andersen, Dana C. and Reilly, Dorothea E., Production technologies for monoclonal antibodies and their fragments, Current Opinion in Biotechnolgoy, 2004, pp. 456-462, vol. 15.

Baldi, Lucia et al., Recombinant protein production by large-scale transient gene expression in mammalian cells: state of the art and future perspectives, Biotechnology Letters, 2007, pp. 677-684, vol. 29.

Baldi, Lucia et al., Transient Gene Expression in Suspension HEK-293 Cells: Application to Large-Scale Protein Production, Biotechnology Progress, 2005, pp. 148-153, vol. 21.

Blend, Michael J. et al., Labeling anti-HER2/neu Monoclonal Antibodies with 111In and 90Y Using a Bifunctional DTPA Chelating Agent, Cancer Biotherapy & Radiopharmaceuticals, 2003, pp. 355-363, vol. 18, No. 3.

Briggs, Mark S. J. et al., Synthesis of functionalised fluorescent dyes and their coupling to amines and amino acids, Journal of the American Chemical Society, Perkin Trans. 1, 1997, pp. 1051-1058.

Browne, Susan M. and Al-Rubeai, Mohamed, Selection methods for high-producing mammalian cell lines, Trends in Biotechnology, 2007, pp. 425-432, vol. 25, No. 9.

Camera, L. et al., Evaluation of a new DTPA-derivative chelator: comparative biodistribution and imaging studies of 111In-labeled B3 monoclonal antibody in athymic mice bearing human epidermoid carcinoma xenografts, Nuclear Medicine and Biology, 1994, pp. 955-962, Abstract only, vol. 21.

Camera, Luigi et al., Comparative biodistribution of indium- and yttrium-labeled B3 monoclonal antibody conjugated to either 2-(p-SCN-Bz)-6-methyl-DTPA (1B4M-DTPA) or 2-(p-SCN-Bz)-1,4,7,10-tetraazacyclododecane tetraacetic acid (2B-DOTA), European Journal of Nuclear Medicine, 1994, pp. 640-646, vol. 21.

Denardo, Gerald L. et al., Comparison of 1,4,7,10-Tetraazacyclododecane-N,N',N'',N'''-tetraacetic acid (DOTA)-Peptide-ChL6, a Novel Immunoconjugate with Catabolizable Linker, to 2-Iminothiolane-2-[p-(Bromoacetamido)benzyl]—DOTA-ChL6 in Breast Cancer Xenografts, Clinical Cancer Research, 1998, pp. 2483-2490, vol. 4.

Dodeigne, C. et al., Chemiluminescence as diagnostic tool. A review, Talanta, 2000, pp. 415-439, vol. 51.

Dyson, Michael R. et al., Production of soluble mammalian proteins in *Escherichia coli*: identification of protein features that correlate with successful expression, BMC Biotechnology, 2004, 18 pp., vol. 4, No. 32.

Girard, Philippe et al., 100-liter transient transfection, Cytotechnology, 2002, pp. 15-21, vol. 38.

Hanes, Jozef and Plückthun, Andreas, In vitro selection and evolution of functional proteins by using ribosome display, Proceedings of the National Academy of Sciences U.S.A., 1997, pp. 4937-4942, vol. 94, No. 10.

Hartman, Standish C. and Mulligan, Richard C., Two dominant-acting selectable markers for gene transfer studies in mammalian cells, Proceedings of the National Academy of Sciences USA, 1988, pp. 8047-8051, vol. 85.

Henikoff, Steven and Henikoff, Jorja G., Amino acid substitution matrices from protein blocks, Proceedings of the National Academy of Sciences USA, 1992, pp. 10915-10919, vol. 89.

Herrera-Estrella, L. et al., Chimeric genes as dominant selectable markers in plant cells, The EMBO Journal, 1983, pp. 987-995, vol. 2, No. 6.

Hinatowich, D.J. et al., The Preparation of DTPA-Coupled Antibodies Radiolabeled with Metallic Radionuclides: an Improved Method, Journal of Immunological Methods, 1983, pp. 147-157, vol. 65.

Izard, M. E. et al., An Improved Method for Labeling Monoclonal Antibodies with Samarium-153: Use of the Bifunctional Chelate 2-(p-Isothiocyanatobenzyl)-6-methyldiethylenetriaminepentaacetic Acid, Bioconjugate Chemistry, 1992, pp. 346-350, vol. 3.

Wurm, Florian M., Production of recombinant protein therapeutics in cultivated mammalian cells, Nature Biotechnology, 2004, pp. 1393-1398, vol. 22, No. 11.

Kobayashi, Hisataka et al., Evaluation of the in Vivo Biodistribution of Indium-111 and Yttrium-88 Labeled Dendrimer-1B4M-DTPA and Its Conjugation with Anti-Tac Monoclonal Antibody, Bioconjugate Chemistry, 1999, pp. 103-111, vol. 10.

Kobayashi, Hisataka et al., Evaluation of the in Vivo Biodistribution of Yttrium-Labeled Isomers of CHX-DTPA-Conjugated Monoclonal Antibodies, Journal of Nuclear Medicine, 1998, pp. 829-836, vol. 39.

Kukis, David L. et al., Optimized Conditions for Chelation of Yttrium-90-DOTA Immunoconjugates, Journal of Nuclear Medicine, 1998, pp. 2105-2110, vol. 39.

Lee, Fook-Thean et al., Specific Localization, Gamma Camera Imaging, and Intracellular Trafficking of Radiolabelled Chimeric Anti-GD3 Ganglioside Monoclonal Antibody KM871 in SK-MEL-28 Melanoma Xenografts, Cancer Research, 2001, pp. 4474-4482, vol. 61.

Mardirossian, G. et al., The stability in liver homogenates of indium-111 and yttrium-90 attached to antibody via Two popular chelators, Nuclear Medicine and Biology, 1993, pp. 65-74, vol. 20, No. 1.

Marsh, J. Lawrence et al., The pIC plasmid and phage vectors with versatile cloning sites for recombinant selection by insertional inactivation, Gene, 1984, pp. 481-485, vol. 32.

Matasci, Mattia et al., Recombinant therapeutic protein production in cultivated mammalian cells: current status and future prospects, Drug Discovery Today: Technologies, 2008, pp. e37-e42, vol. 5, No. 2-3.

Meares, C F. et al., Macrocyclic chelates of radiometals for diagnosis and therapy, British Journal of Cancer, 1990, pp. 21-26, vol. 62, Supp X.

Meares, Claude F. et al., Conjugation of Antibodies with Bifunctional Chelating Agents: Isothiocyanate and Bromoacetamide Reagents, Methods of Analysis, and Subsequent Addition of Metal Ions, Analytical Biochemistry, 1984, pp. 68-78, vol. 142.

Miederer, Matthias et al., Pharmacokinetics, Dosimetry, and Toxicity of the Targetable Atomic Generator, 225Ac-HuM195, in Non-human Primates, Journal of Nuclear Medicine, 2004, pp. 129-137, vol. 45.

Mirzadeh, Saed et al., Radiometal Labeling of Immunoproteins: Covalent Linkage of 2-(4-Isothiocyanatobenzyl) diethylenetriaminepentaacetic Acid Ligands to Immunoglobulin, Bioconjugate Chemistry, 1990, pp. 59-65, vol. 1.

Mitchell, Paul et al., Targeting Primary Human Ph+ B-Cell Precursor Leukemia-Engrafted SCID Mice Using Radiolabeled Anti-CD19 Monoclonal Antibodies, Journal of Nuclear Medicine, 2003, pp. 1105-1112, vol. 44.

Nikula, Tuomo K. et al., A Rapid, Single Vessel Method for Preparation of Clinical Grade Ligand Conjugated Monoclonal Antibodies, Nuclear Medicine and Biology, 1995, pp. 387-390, vol. 22, No. 3.

Nikula, Tuomo K. et al., Alpha-Emitting Bismuth Cyclohexylbenzyl DTPA Constructs of Recombinant Humanized Anti-CD33 Antibod-

(56) References Cited

OTHER PUBLICATIONS ies: Pharmacokinetics, Bioactivity, Toxicity and Chemistry, Journal of Nuclear Medicine, 1999, pp. 166-176, vol. 40.
Norderhaug, Lars et al., Versatile vectors for transient and stable expression of recombinant antibody molecules in mammalian cells, Journal of Immunological Methods, 1997, pp. 77-87, vol. 204.
Owens, Geoffrey C. et al., Identification of two short internal ribosome entry sites selected from libraries of random oligonucleotides, Proceedings of the National Academy of Sciences USA, 2001, pp. 1471-1476, vol. 98, No. 4.
Pearson, William R. and Lipman, David J., "Improved tools for biological sequence comparison", Proceedings of the National Academy of Sciences USA, 1988, pp. 2444-2448, vol. 85.
Plückthun, A., Antibodies from *Escherichia coli*, The Pharmacology of Monoclonal Antibodies, 1994, pp. 269-315, vol. 113, Chapter 11, Springer-Verlag, New York.
Reiss, Bernd et al., A family of binary gene vectors with low inter-transformant variation, Plant Physiology (Life Science Advances), 1994, pp. 143-149, vol. 13.
Roselli, Mario et al., In Vivo Comparison of CHX-DTPA Ligand Isomers in Athymic Mice Bearing Carcinoma Kernografts, Cancer Biotherapy & Radiopharmaceuticals, 1999, pp. 209-220, vol. 14, No. 3.
Ruegg, Curtis L. et al., Improved in Vivo Stability and Tumor Targeting of Bismuth-labeled Antibody, Cancer Research, 1990, pp. 4221-4226, vol. 50.
Schräml, Michael and Biehl, Matthias, Kinetic Screening in the Antibody Development Process, Methods in Molecular Biology, 2012, pp. 171-181, vol. 901, Ch. 11.
Simmons, Lara C. et al., Expression of full-length immunoglobulins in *Escherichia coli*: rapid and efficient production of aglycosylated antibodies, Journal of Immunological Methods, 2002, pp. 133-147, vol. 263.
Staffilani, Mara et al., Multimetallic Ruthenium(II) Complexes as Electrochemiluminescent Labels, Inorganic Chemistry, 2003, pp. 7789-7798, vol. 42.
Stettler, Matthieu et al., Novel Orbital Shake Bioreactors for Transient Production of CHO Derived IgGs, Biotechnology Progress, 2007, pp. 1340-1346, vol. 23.
Tamura, Katsunori et al., Blasticidin S Deaminase Gene (BSD): a New Selection Marker Gene for Transformation of Arabidopsis thaliana and Nicotiana tabacum, Bioscience, Biotechnology, and Biochemistry, 1995, pp. 2336-2338, vol. 59, No. 12.
Thompson, Julie D. et al., CLUSTAL W: improving the sensitivity of progressive multiple sequence alignment through sequence weighting, position-specific gap penalties and weight matrix choice, Nucleic Acids Research, 1994, pp. 4673-4680, vol. 22, No. 22.
Verel, Iris et al., Quantitative 89Zr Immuno-PET for In Vivo Scouting of 90Y-Labeled Monoclonal Antibodies in Kenograft-Bearing Nude Mice, Journal of Nuclear Medicine, 2003, pp. 1663-1670, vol. 44.
Westermann, Dirk et al., High-sensitivity assays for troponin in patients with cardiac disease, Nature Reviews Cardiology, 2017, pp. 472-483, vol. 14.
Hu et al., Effective Optimization of Antibody Affinity by Phage Display Integrated with High-Throughput DNA Synthesis and Sequencing Technologies; PLOS one; Jun. 5, 2015, vol. 10, No. 6, pp. e0129125 (17-pages).

* cited by examiner

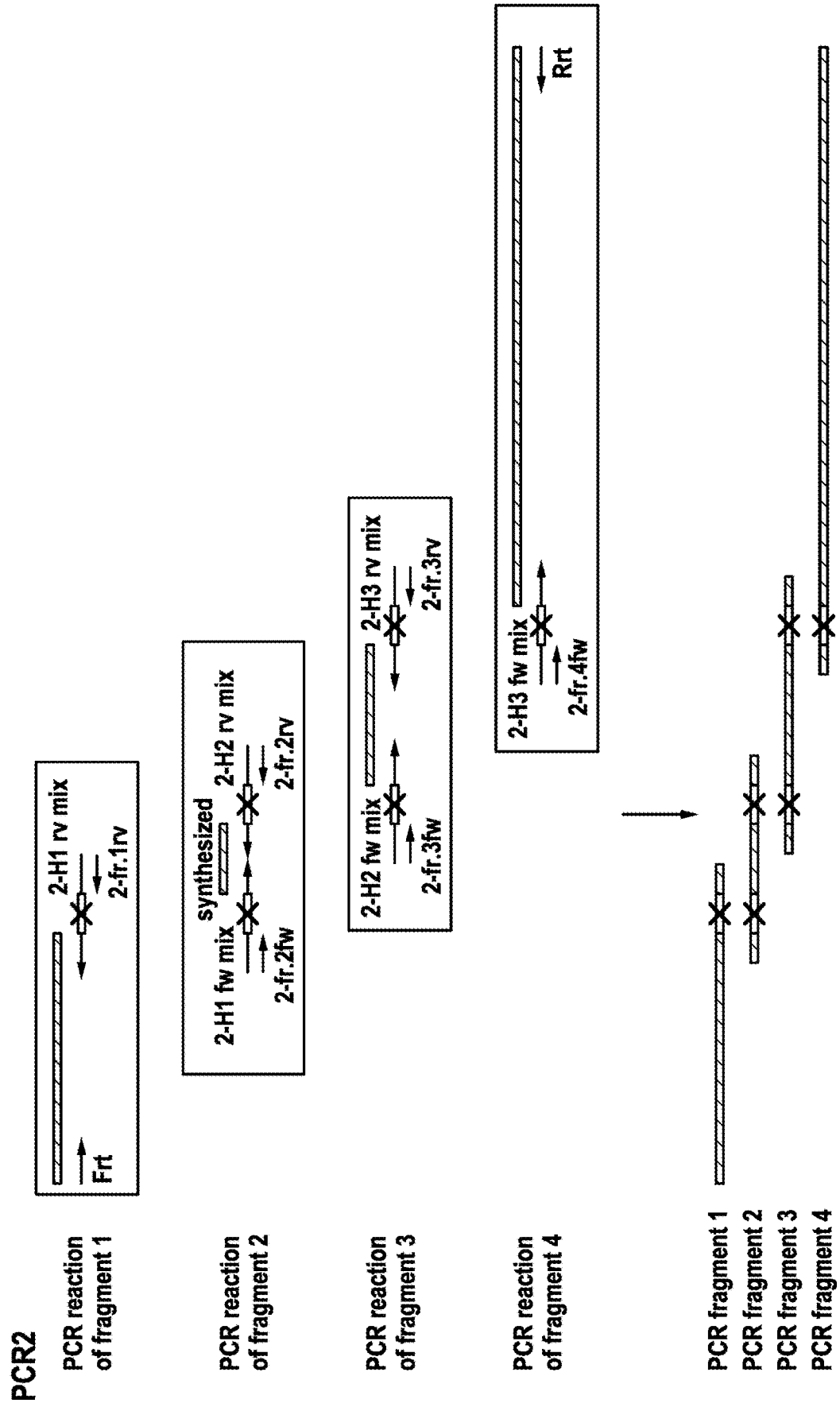

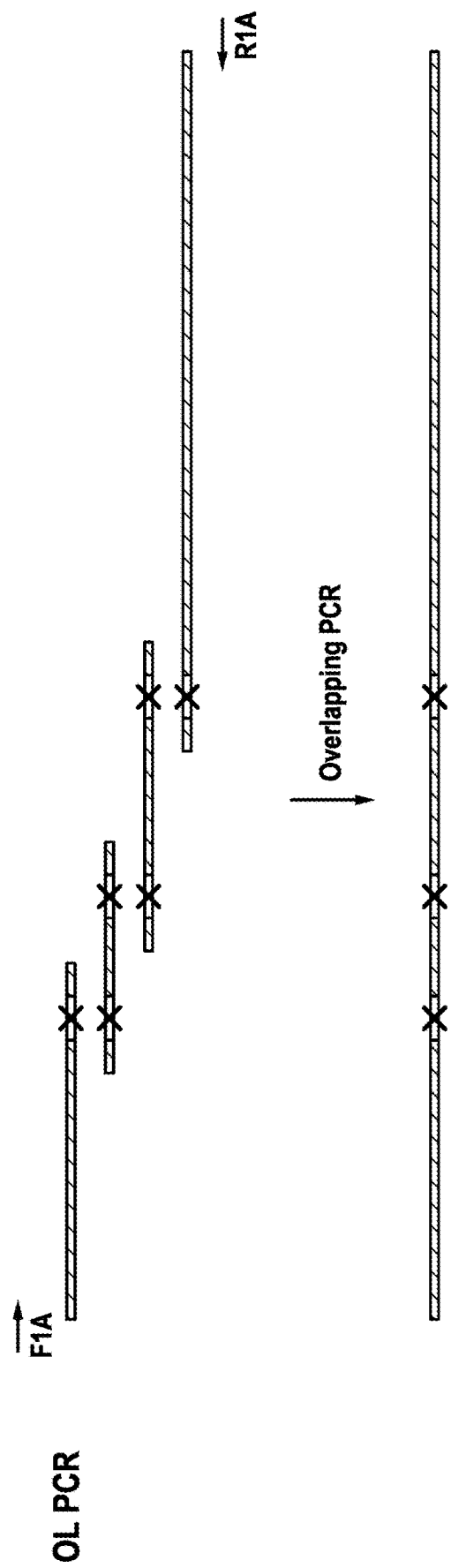

SEQUENCE LISTING

<160> NUMBER OF SEQ ID NOS: 95

<210> SEQ ID NO 1
<211> LENGTH: 297
<212> TYPE: PRT
<213> ORGANISM: homo sapiens

<400> SEQUENCE: 1

Met Ser Asp Ile Glu Glu Val Val Glu Tyr Glu Glu Glu Gln
1               5                   10                  15
Glu Glu Ala Ala Val Glu Glu Glu Asp Trp Arg Glu Asp Asp
                20                  25                  30
Glu Gln Glu Glu Ala Ala Glu Asp Ala Glu Ala Glu Thr
            35                  40                  45
Glu Glu Thr Arg Ala Glu Asp Glu Glu Glu Glu Ala Lys Glu
    50                  55                  60
Ala Glu Asp Gly Pro Met Glu Glu Ser Lys Pro Lys Pro Arg Ser Phe
65                  70                      75                  80
Met Pro Asn Leu Val Pro Pro Lys Ile Pro Asp Gly Glu Arg Val Asp
                85                  90                  95
Phe Asp Asp Ile His Arg Lys Arg Met Glu Lys Asp Leu Asn Glu Leu
                100                 105                 110
Gln Ala Leu Ile Glu Ala His Phe Glu Asn Arg Lys Lys Glu Glu Glu
                115                 120                 125
Glu Leu Val Ser Leu Lys Asp Arg Ile Glu Arg Arg Ala Glu Arg
                130                 135                 140
Ala Glu Gln Gln Arg Ile Arg Asn Glu Arg Glu Lys Glu Arg Gln Asn
145                 150                 155                 160
Arg Leu Ala Glu Glu Arg Ala Arg Arg Glu Glu Glu Asn Arg Arg
                165                 170                 175
Lys Ala Glu Asp Ala Arg Lys Lys Ala Leu Ser Asn Met Met His
                180                 185                 190
Phe Gly Gly Tyr Ile Gln Lys Gln Ala Gln Thr Glu Arg Lys Ser Gly
                195                 200                 205
Lys Arg Gln Thr Glu Arg Glu Lys Lys Lys Ile Leu Ala Glu Arg
                210                 215                 220
Arg Lys Val Leu Ala Ile Asp His Leu Asn Glu Asp Gln Leu Arg Glu
225                 230                 235                 240
Lys Ala Lys Glu Leu Trp Gln Ser Ile Tyr Asn Leu Glu Ala Glu Lys
                245                 250                 255
Phe Asp Leu Gln Glu Lys Phe Lys Gln Gln Lys Tyr Glu Ile Asn Val
                260                 265                 270
Leu Arg Asn Arg Ile Asn Asp Asn Gln Lys Val Ser Lys Thr Arg Gly
                275                 280                 285
Lys Ala Lys Val Thr Gly Arg Trp Lys
290                 295

<210> SEQ ID NO 2
<211> LENGTH: 15
<212> TYPE: PRT
<213> ORGANISM: mus musculus

<400> SEQUENCE: 2

Lys Ala Ser Gln Ser Val Asp Tyr Asp Gly Thr Ser Tyr Met Asn
1               5                   10                  15

<210> SEQ ID NO 3
<211> LENGTH: 7
<212> TYPE: PRT
<213> ORGANISM: mus musculus

<400> SEQUENCE: 3

Ala Ala Ser Asn Leu Glu Ser

```
<210> SEQ ID NO 4
<211> LENGTH: 9
<212> TYPE: PRT
<213> ORGANISM: mus musculus

<400> SEQUENCE: 4

Gln Gln Ser Asn Glu Asp Pro Tyr Thr
1               5

<210> SEQ ID NO 5
<211> LENGTH: 5
<212> TYPE: PRT
<213> ORGANISM: mus musculus

<400> SEQUENCE: 5

Asp Tyr Tyr Met Lys
1               5

<210> SEQ ID NO 6
<211> LENGTH: 5
<212> TYPE: PRT
<213> ORGANISM: Mus musculus

<400> SEQUENCE: 6

Asp Tyr Ile Met Lys
1               5

<210> SEQ ID NO 7
<211> LENGTH: 5
<212> TYPE: PRT
<213> ORGANISM: mus musculus

<400> SEQUENCE: 7

Asp Tyr Phe Met Lys
1               5

<210> SEQ ID NO 8
<211> LENGTH: 10
<212> TYPE: PRT
<213> ORGANISM: mus musculus

<400> SEQUENCE: 8

Asp Ile Asn Pro Asn Asn Gly Glu Thr Phe
1               5                   10

<210> SEQ ID NO 9
<211> LENGTH: 10
<212> TYPE: PRT
<213> ORGANISM: mus musculus

<400> SEQUENCE: 9

Asp Ile Asn Pro Asn Asn Gly Glu Thr Trp
1               5                   10

<210> SEQ ID NO 10
<211> LENGTH: 5
<212> TYPE: PRT
<213> ORGANISM: mus musculus

<400> SEQUENCE: 10

Arg Val Phe Asp Tyr
1               5
```

```
<210> SEQ ID NO 11
<211> LENGTH: 5
<212> TYPE: PRT
<213> ORGANISM: mus musculus

<400> SEQUENCE: 11

Arg Tyr Phe Asp Tyr
1               5

<210> SEQ ID NO 12
<211> LENGTH: 5
<212> TYPE: PRT
<213> ORGANISM: mus musculus

<400> SEQUENCE: 12

Arg Val Phe Asp Phe
1               5

<210> SEQ ID NO 13
<211> LENGTH: 5
<212> TYPE: PRT
<213> ORGANISM: mus musculus

<400> SEQUENCE: 13

Arg Tyr Phe Asp Phe
1               5

<210> SEQ ID NO 14
<211> LENGTH: 24
<212> TYPE: PRT
<213> ORGANISM: mus musculus

<400> SEQUENCE: 14

Met Asp Ile Val Leu Thr Gln Ser Pro Ala Ser Leu Ala Val Ser Leu
1               5                   10                  15

Gly Gln Arg Ala Thr Ile Ser Cys
            20

<210> SEQ ID NO 15
<211> LENGTH: 15
<212> TYPE: PRT
<213> ORGANISM: mus musculus

<400> SEQUENCE: 15

Trp Phe Gln Gln Lys Ala Gly Gln Pro Pro Lys Arg Leu Ile Tyr
1               5                   10                  15

<210> SEQ ID NO 16
<211> LENGTH: 32
<212> TYPE: PRT
<213> ORGANISM: mus musculus

<400> SEQUENCE: 16

Gly Ile Pro Ala Arg Phe Ser Gly Arg Gly Ser Gly Thr Asp Phe Ala
1               5                   10                  15

Leu Asn Ile His Pro Val Glu Glu Glu Asp Ala Ala Thr Tyr Tyr Cys
            20                  25                  30

<210> SEQ ID NO 17
<211> LENGTH: 11
<212> TYPE: PRT
<213> ORGANISM: mus musculus

<400> SEQUENCE: 17
```

```
Phe Gly Gly Gly Thr Lys Leu Glu Ile Lys Arg
1               5                   10
```

<210> SEQ ID NO 18
<211> LENGTH: 31
<212> TYPE: PRT
<213> ORGANISM: mus musculus

<400> SEQUENCE: 18

```
Met Glu Val Gln Leu Gln Gln Ser Gly Pro Glu Leu Val Lys Pro Gly
1               5                   10                  15

Ala Ser Val Lys Met Ser Cys Lys Ala Ser Gly Tyr Thr Phe Thr
            20                  25                  30
```

<210> SEQ ID NO 19
<211> LENGTH: 14
<212> TYPE: PRT
<213> ORGANISM: mus musculus

<400> SEQUENCE: 19

```
Trp Val Lys Gln Ser His Gly Lys Ser Leu Glu Trp Ile Gly
1               5                   10
```

<210> SEQ ID NO 20
<211> LENGTH: 39
<212> TYPE: PRT
<213> ORGANISM: mus musculus

<400> SEQUENCE: 20

```
Tyr Asn Gln Lys Phe Lys Asp Lys Ala Thr Leu Thr Val Asp Lys Ser
1               5                   10                  15

Ser Ser Thr Ala Tyr Met Gln Leu Asn Ser Leu Thr Ser Glu Asp Ser
            20                  25                  30

Ala Val Tyr Tyr Cys Ala Thr
            35
```

<210> SEQ ID NO 21
<211> LENGTH: 11
<212> TYPE: PRT
<213> ORGANISM: mus musculus

<400> SEQUENCE: 21

```
Trp Gly Gln Gly Thr Thr Leu Thr Val Ser Ser
1               5                   10
```

<210> SEQ ID NO 22
<211> LENGTH: 219
<212> TYPE: PRT
<213> ORGANISM: mus musculus

<400> SEQUENCE: 22

```
Met Asp Ile Val Leu Thr Gln Ser Pro Ala Ser Leu Ala Val Ser Leu
1               5                   10                  15

Gly Gln Arg Ala Thr Ile Ser Cys Lys Ala Ser Gln Ser Val Asp Tyr
            20                  25                  30

Asp Gly Thr Ser Tyr Met Asn Trp Phe Gln Gln Lys Ala Gly Gln Pro
        35                  40                  45

Pro Lys Arg Leu Ile Tyr Ala Ala Ser Asn Leu Glu Ser Gly Ile Pro
    50                  55                  60

Ala Arg Phe Ser Gly Arg Gly Ser Gly Thr Asp Phe Ala Leu Asn Ile
65                  70                  75                  80
```

His Pro Val Glu Glu Asp Ala Ala Thr Tyr Tyr Cys Gln Gln Ser
                85                  90                  95

Asn Glu Asp Pro Tyr Thr Phe Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
        210                 215

<210> SEQ ID NO 23
<211> LENGTH: 212
<212> TYPE: PRT
<213> ORGANISM: mus musculus

<400> SEQUENCE: 23

Met Glu Val Gln Leu Gln Gln Ser Gly Pro Glu Leu Val Lys Pro Gly
1               5                   10                  15

Ala Ser Val Lys Met Ser Cys Lys Ala Ser Gly Tyr Thr Phe Thr Asp
            20                  25                  30

Tyr Ile Met Lys Trp Val Lys Gln Ser His Gly Lys Ser Leu Glu Trp
        35                  40                  45

Ile Gly Asp Ile Asn Pro Asn Asn Gly Glu Thr Trp Tyr Asn Gln Lys
    50                  55                  60

Phe Lys Asp Lys Ala Thr Leu Thr Val Asp Lys Ser Ser Ser Thr Ala
65                  70                  75                  80

Tyr Met Gln Leu Asn Ser Leu Thr Ser Glu Asp Ser Ala Val Tyr Tyr
                85                  90                  95

Cys Ala Thr Arg Val Phe Asp Phe Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile
    210

-continued

```
<210> SEQ ID NO 24
<211> LENGTH: 212
<212> TYPE: PRT
<213> ORGANISM: mus musculus

<400> SEQUENCE: 24

Met Glu Val Gln Leu Gln Gln Ser Gly Pro Glu Leu Val Lys Pro Gly
1               5                   10                  15

Ala Ser Val Lys Met Ser Cys Lys Ala Ser Gly Tyr Thr Phe Thr Asp
            20                  25                  30

Tyr Phe Met Lys Trp Val Lys Gln Ser His Gly Lys Ser Leu Glu Trp
        35                  40                  45

Ile Gly Asp Ile Asn Pro Asn Asn Gly Glu Thr Phe Tyr Asn Gln Lys
    50                  55                  60

Phe Lys Asp Lys Ala Thr Leu Thr Val Asp Lys Ser Ser Ser Thr Ala
65                  70                  75                  80

Tyr Met Gln Leu Asn Ser Leu Thr Ser Glu Asp Ser Ala Val Tyr Tyr
                85                  90                  95

Cys Ala Thr Arg Tyr Phe Asp Tyr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile
    210

<210> SEQ ID NO 25
<211> LENGTH: 212
<212> TYPE: PRT
<213> ORGANISM: mus musculus

<400> SEQUENCE: 25

Met Glu Val Gln Leu Gln Gln Ser Gly Pro Glu Leu Val Lys Pro Gly
1               5                   10                  15

Ala Ser Val Lys Met Ser Cys Lys Ala Ser Gly Tyr Thr Phe Thr Asp
            20                  25                  30

Tyr Phe Met Lys Trp Val Lys Gln Ser His Gly Lys Ser Leu Glu Trp
        35                  40                  45

Ile Gly Asp Ile Asn Pro Asn Asn Gly Glu Thr Phe Tyr Asn Gln Lys
    50                  55                  60

Phe Lys Asp Lys Ala Thr Leu Thr Val Asp Lys Ser Ser Ser Thr Ala
65                  70                  75                  80

Tyr Met Gln Leu Asn Ser Leu Thr Ser Glu Asp Ser Ala Val Tyr Tyr
                85                  90                  95

Cys Ala Thr Arg Tyr Phe Asp Phe Trp Gly Gln Gly Thr Thr Leu Thr
            100                 105                 110

Val Ser Ser Ala Lys Thr Thr Pro Pro Ser Val Tyr Pro Leu Ala Pro
```

```
            115                 120                 125
Gly Ser Ala Ala Gln Thr Asn Ser Met Val Thr Leu Gly Cys Leu Val
    130                 135                 140
Lys Gly Tyr Phe Pro Glu Pro Val Thr Val Thr Trp Asn Ser Gly Ser
145                 150                 155                 160
Leu Ser Ser Gly Val His Thr Phe Pro Ala Val Leu Gln Ser Asp Leu
                165                 170                 175
Tyr Thr Leu Ser Ser Ser Val Thr Val Pro Ser Ser Thr Trp Pro Ser
            180                 185                 190
Glu Thr Val Thr Cys Asn Val Ala His Pro Ala Ser Ser Thr Lys Val
                195                 200                 205
Asp Lys Lys Ile
        210

<210> SEQ ID NO 26
<211> LENGTH: 212
<212> TYPE: PRT
<213> ORGANISM: mus musculus

<400> SEQUENCE: 26

Met Glu Val Gln Leu Gln Gln Ser Gly Pro Glu Leu Val Lys Pro Gly
1               5                   10                  15
Ala Ser Val Lys Met Ser Cys Lys Ala Ser Gly Tyr Thr Phe Thr Asp
            20                  25                  30
Tyr Phe Met Lys Trp Val Lys Gln Ser His Gly Lys Ser Leu Glu Trp
        35                  40                  45
Ile Gly Asp Ile Asn Pro Asn Asn Gly Glu Thr Trp Tyr Asn Gln Lys
    50                  55                  60
Phe Lys Asp Lys Ala Thr Leu Thr Val Asp Lys Ser Ser Ser Thr Ala
65                  70                  75                  80
Tyr Met Gln Leu Asn Ser Leu Thr Ser Glu Asp Ser Ala Val Tyr Tyr
                85                  90                  95
Cys Ala Thr Arg Tyr Phe Asp Phe Trp Gly Gln Gly Thr Thr Leu Thr
            100                 105                 110
Val Ser Ser Ala Lys Thr Thr Pro Pro Ser Val Tyr Pro Leu Ala Pro
        115                 120                 125
Gly Ser Ala Ala Gln Thr Asn Ser Met Val Thr Leu Gly Cys Leu Val
    130                 135                 140
Lys Gly Tyr Phe Pro Glu Pro Val Thr Val Thr Trp Asn Ser Gly Ser
145                 150                 155                 160
Leu Ser Ser Gly Val His Thr Phe Pro Ala Val Leu Gln Ser Asp Leu
                165                 170                 175
Tyr Thr Leu Ser Ser Ser Val Thr Val Pro Ser Ser Thr Trp Pro Ser
            180                 185                 190
Glu Thr Val Thr Cys Asn Val Ala His Pro Ala Ser Ser Thr Lys Val
                195                 200                 205
Asp Lys Lys Ile
        210

<210> SEQ ID NO 27
<211> LENGTH: 212
<212> TYPE: PRT
<213> ORGANISM: mus musculus

<400> SEQUENCE: 27

Met Glu Val Gln Leu Gln Gln Ser Gly Pro Glu Leu Val Lys Pro Gly
```

```
                1               5                      10                     15
            Ala Ser Val Lys Met Ser Cys Lys Ala Ser Gly Tyr Thr Phe Thr Asp
                            20                  25                  30
            Tyr Phe Met Lys Trp Val Lys Gln Ser His Gly Lys Ser Leu Glu Trp
                            35                  40                  45
            Ile Gly Asp Ile Asn Pro Asn Asn Gly Glu Thr Trp Tyr Asn Gln Lys
                50                      55                      60
            Phe Lys Asp Lys Ala Thr Leu Thr Val Asp Lys Ser Ser Ser Thr Ala
            65                      70                      75                  80
            Tyr Met Gln Leu Asn Ser Leu Thr Ser Glu Asp Ser Ala Val Tyr Tyr
                            85                  90                  95
            Cys Ala Thr Arg Tyr Phe Asp Tyr Trp Gly Gln Gly Thr Thr Leu Thr
                            100                 105                 110
            Val Ser Ser Ala Lys Thr Thr Pro Pro Ser Val Tyr Pro Leu Ala Pro
                            115                 120                 125
            Gly Ser Ala Ala Gln Thr Asn Ser Met Val Thr Leu Gly Cys Leu Val
                        130                 135                 140
            Lys Gly Tyr Phe Pro Glu Pro Val Thr Val Thr Trp Asn Ser Gly Ser
            145                 150                     155                 160
            Leu Ser Ser Gly Val His Thr Phe Pro Ala Val Leu Gln Ser Asp Leu
                            165                 170                 175
            Tyr Thr Leu Ser Ser Ser Val Thr Val Pro Ser Ser Thr Trp Pro Ser
                            180                 185                 190
            Glu Thr Val Thr Cys Asn Val Ala His Pro Ala Ser Ser Thr Lys Val
                            195                 200                 205
            Asp Lys Lys Ile
                        210

<210> SEQ ID NO 28
<211> LENGTH: 212
<212> TYPE: PRT
<213> ORGANISM: mus musculus

<400> SEQUENCE: 28

Met Glu Val Gln Leu Gln Gln Ser Gly Pro Glu Leu Val Lys Pro Gly
            1               5                       10                      15
            Ala Ser Val Lys Met Ser Cys Lys Ala Ser Gly Tyr Thr Phe Thr Asp
                            20                  25                  30
            Tyr Phe Met Lys Trp Val Lys Gln Ser His Gly Lys Ser Leu Glu Trp
                            35                  40                  45
            Ile Gly Asp Ile Asn Pro Asn Asn Gly Glu Thr Trp Tyr Asn Gln Lys
                50                      55                      60
            Phe Lys Asp Lys Ala Thr Leu Thr Val Asp Lys Ser Ser Ser Thr Ala
            65                      70                      75                  80
            Tyr Met Gln Leu Asn Ser Leu Thr Ser Glu Asp Ser Ala Val Tyr Tyr
                            85                  90                  95
            Cys Ala Thr Arg Val Phe Asp Phe Trp Gly Gln Gly Thr Thr Leu Thr
                            100                 105                 110
            Val Ser Ser Ala Lys Thr Thr Pro Pro Ser Val Tyr Pro Leu Ala Pro
                            115                 120                 125
            Gly Ser Ala Ala Gln Thr Asn Ser Met Val Thr Leu Gly Cys Leu Val
                        130                 135                 140
            Lys Gly Tyr Phe Pro Glu Pro Val Thr Val Thr Trp Asn Ser Gly Ser
            145                 150                     155                 160
```

```
Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile
    210
```

<210> SEQ ID NO 29
<211> LENGTH: 212
<212> TYPE: PRT
<213> ORGANISM: mus musculus

<400> SEQUENCE: 29

```
Met Glu Val Gln Leu Gln Gln Ser Gly Pro Glu Leu Val Lys Pro Gly
1               5                   10                  15

Ala Ser Val Lys Met Ser Cys Lys Ala Ser Gly Tyr Thr Phe Thr Asp
            20                  25                  30

Tyr Phe Met Lys Trp Val Lys Gln Ser His Gly Lys Ser Leu Glu Trp
        35                  40                  45

Ile Gly Asp Ile Asn Pro Asn Asn Gly Glu Thr Trp Tyr Asn Gln Lys
    50                  55                  60

Phe Lys Asp Lys Ala Thr Leu Thr Val Asp Lys Ser Ser Ser Thr Ala
65                  70                  75                  80

Tyr Met Gln Leu Asn Ser Leu Thr Ser Glu Asp Ser Ala Val Tyr Tyr
                85                  90                  95

Cys Ala Thr Arg Val Phe Asp Tyr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile
    210
```

<210> SEQ ID NO 30
<211> LENGTH: 212
<212> TYPE: PRT
<213> ORGANISM: mus musculus

<400> SEQUENCE: 30

```
Met Glu Val Gln Leu Gln Gln Ser Gly Pro Glu Leu Val Lys Pro Gly
1               5                   10                  15

Ala Ser Val Lys Met Ser Cys Lys Ala Ser Gly Tyr Thr Phe Thr Asp
            20                  25                  30

Tyr Phe Met Lys Trp Val Lys Gln Ser His Gly Lys Ser Leu Glu Trp
        35                  40                  45
```

```
Ile Gly Asp Ile Asn Pro Asn Asn Gly Glu Thr Phe Tyr Asn Gln Lys
 50                  55                  60

Phe Lys Asp Lys Ala Thr Leu Thr Val Asp Lys Ser Ser Ser Thr Ala
 65                  70                  75                  80

Tyr Met Gln Leu Asn Ser Leu Thr Ser Glu Asp Ser Ala Val Tyr Tyr
                 85                  90                  95

Cys Ala Thr Arg Val Phe Asp Phe Trp Gly Gln Gly Thr Thr Leu Thr
                100                 105                 110

Val Ser Ser Ala Lys Thr Thr Pro Pro Ser Val Tyr Pro Leu Ala Pro
            115                 120                 125

Gly Ser Ala Ala Gln Thr Asn Ser Met Val Thr Leu Gly Cys Leu Val
        130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
                195                 200                 205

Asp Lys Lys Ile
        210

<210> SEQ ID NO 31
<211> LENGTH: 212
<212> TYPE: PRT
<213> ORGANISM: mus musculus

<400> SEQUENCE: 31

Met Glu Val Gln Leu Gln Gln Ser Gly Pro Glu Leu Val Lys Pro Gly
  1               5                  10                  15

Ala Ser Val Lys Met Ser Cys Lys Ala Ser Gly Tyr Thr Phe Thr Asp
                 20                  25                  30

Tyr Tyr Met Lys Trp Val Lys Gln Ser His Gly Lys Ser Leu Glu Trp
             35                  40                  45

Ile Gly Asp Ile Asn Pro Asn Asn Gly Glu Thr Trp Tyr Asn Gln Lys
 50                  55                  60

Phe Lys Asp Lys Ala Thr Leu Thr Val Asp Lys Ser Ser Ser Thr Ala
 65                  70                  75                  80

Tyr Met Gln Leu Asn Ser Leu Thr Ser Glu Asp Ser Ala Val Tyr Tyr
                 85                  90                  95

Cys Ala Thr Arg Val Phe Asp Phe Trp Gly Gln Gly Thr Thr Leu Thr
                100                 105                 110

Val Ser Ser Ala Lys Thr Thr Pro Pro Ser Val Tyr Pro Leu Ala Pro
            115                 120                 125

Gly Ser Ala Ala Gln Thr Asn Ser Met Val Thr Leu Gly Cys Leu Val
        130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
                195                 200                 205
```

```
Asp Lys Lys Ile
    210

<210> SEQ ID NO 32
<211> LENGTH: 212
<212> TYPE: PRT
<213> ORGANISM: mus musculus

<400> SEQUENCE: 32

Met Glu Val Gln Leu Gln Gln Ser Gly Pro Glu Leu Val Lys Pro Gly
1               5                   10                  15

Ala Ser Val Lys Met Ser Cys Lys Ala Ser Gly Tyr Thr Phe Thr Asp
            20                  25                  30

Tyr Ile Met Lys Trp Val Lys Gln Ser His Gly Lys Ser Leu Glu Trp
        35                  40                  45

Ile Gly Asp Ile Asn Pro Asn Asn Gly Glu Thr Trp Tyr Asn Gln Lys
    50                  55                  60

Phe Lys Asp Lys Ala Thr Leu Thr Val Asp Lys Ser Ser Ser Thr Ala
65                  70                  75                  80

Tyr Met Gln Leu Asn Ser Leu Thr Ser Glu Asp Ser Ala Val Tyr Tyr
                85                  90                  95

Cys Ala Thr Arg Val Phe Asp Tyr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile
    210

<210> SEQ ID NO 33
<211> LENGTH: 210
<212> TYPE: PRT
<213> ORGANISM: homo sapiens

<400> SEQUENCE: 33

Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45

Leu Lys Thr Leu Leu Leu Gln Ile Ala Lys Gln Glu Leu Glu Arg Glu
    50                  55                  60

Ala Glu Glu Arg Arg Gly Glu Lys Gly Arg Ala Leu Ser Thr Arg Cys
65                  70                  75                  80

Gln Pro Leu Glu Leu Ala Gly Leu Gly Phe Ala Glu Leu Gln Asp Leu
                85                  90                  95
```

Cys Arg Gln Leu His Ala Arg Val Asp Lys Val Asp Glu Arg Tyr
            100                 105                 110

Asp Ile Glu Ala Lys Val Thr Lys Asn Ile Thr Glu Ile Ala Asp Leu
        115                 120                 125

Thr Gln Lys Ile Phe Asp Leu Arg Gly Lys Phe Lys Arg Pro Thr Leu
130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Phe
        195                 200                 205

Glu Ser
    210

<210> SEQ ID NO 34
<211> LENGTH: 212
<212> TYPE: PRT
<213> ORGANISM: mus musculus

<400> SEQUENCE: 34

Met Glu Val Gln Leu Gln Gln Ser Gly Pro Glu Leu Val Lys Pro Gly
1               5                   10                  15

Ala Ser Val Lys Met Ser Cys Lys Ala Ser Gly Tyr Thr Phe Thr Asp
            20                  25                  30

Tyr Tyr Met Lys Trp Val Lys Gln Ser His Gly Lys Ser Leu Glu Trp
        35                  40                  45

Ile Gly Asp Ile Asn Pro Asn Asn Gly Glu Thr Phe Tyr Asn Gln Lys
    50                  55                  60

Phe Lys Asp Lys Ala Thr Leu Thr Val Asp Lys Ser Ser Ser Thr Ala
65                  70                  75                  80

Tyr Met Gln Leu Asn Ser Leu Thr Ser Glu Asp Ser Ala Val Tyr Tyr
                85                  90                  95

Cys Ala Thr Arg Val Phe Asp Tyr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile
    210

<210> SEQ ID NO 35
<211> LENGTH: 44
<212> TYPE: DNA

```
<213> ORGANISM: artificial sequence
<220> FEATURE:
<223> OTHER INFORMATION: synthetic polynucleotide

<400> SEQUENCE: 35
cgaaattaat acgactcact atagggagac cacaacggtt tccc               44

<210> SEQ ID NO 36
<211> LENGTH: 20
<212> TYPE: DNA
<213> ORGANISM: artificial sequence
<220> FEATURE:
<223> OTHER INFORMATION: synthetic polynucleotide

<400> SEQUENCE: 36
ggtaaaggta tagccgctcg                                          20

<210> SEQ ID NO 37
<211> LENGTH: 26
<212> TYPE: DNA
<213> ORGANISM: artificial sequence
<220> FEATURE:
<223> OTHER INFORMATION: synthetic polynucleotide

<400> SEQUENCE: 37
ccagaaattt aaggataaag cgaccc                                   26

<210> SEQ ID NO 38
<211> LENGTH: 20
<212> TYPE: DNA
<213> ORGANISM: artificial sequence
<220> FEATURE:
<223> OTHER INFORMATION: synthetic polynucleotide

<400> SEQUENCE: 38
ggtcgcgcaa taatacaccg                                          20

<210> SEQ ID NO 39
<211> LENGTH: 20
<212> TYPE: DNA
<213> ORGANISM: artificial sequence
<220> FEATURE:
<223> OTHER INFORMATION: synthetic polynucleotide

<400> SEQUENCE: 39
cggtgtatta ttgcgcgacc                                          20

<210> SEQ ID NO 40
<211> LENGTH: 47
<212> TYPE: DNA
<213> ORGANISM: artificial sequence
<220> FEATURE:
<223> OTHER INFORMATION: synthetic polynucleotide

<400> SEQUENCE: 40 aaccccgca taggctgggg gttggaaagc ctctgaggac cagcacg              47

<210> SEQ ID NO 41
<211> LENGTH: 63
<212> TYPE: DNA
<213> ORGANISM: artificial sequence
<220> FEATURE:
<223> OTHER INFORMATION: synthetic polynucleotide

<400> SEQUENCE: 41
gggagaccac aacggtttcc ctctagaaat aattttgttt aactttaaga aggagatata  60
``` cat                                                              63

<210> SEQ ID NO 42
<211> LENGTH: 44
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (29)..(30)
<223> OTHER INFORMATION: n is a, c, g, or t

<400> SEQUENCE: 42
gctctgtttc acccatttca tataatamnn ggtaaaggta tagc              44

<210> SEQ ID NO 43
<211> LENGTH: 44
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (26)..(27)
<223> OTHER INFORMATION: n is a, c, g, or t

<400> SEQUENCE: 43
gctctgtttc acccatttca tatamnnatc ggtaaaggta tagc              44

<210> SEQ ID NO 44
<211> LENGTH: 44
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (22)..(23)
<223> OTHER INFORMATION: n is a, c, g, or t

<400> SEQUENCE: 44
gctctgtttc acccatttca mnnaataatc ggtaaaggta tagc              44

<210> SEQ ID NO 45
<211> LENGTH: 44
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (20)..(21)
<223> OTHER INFORMATION: n is a, c, g, or t

<400> SEQUENCE: 45
gctctgtttc acccatttmn nataataatc ggtaaaggta tagc              44

<210> SEQ ID NO 46
<211> LENGTH: 44
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (17)..(18)
<223> OTHER INFORMATION: n is a, c, g, or t

<400> SEQUENCE: 46
gctctgtttc acccamnnca tataataatc ggtaaaggta tagc                44

<210> SEQ ID NO 47
<211> LENGTH: 19
<212> TYPE: DNA
<213> ORGANISM: artificial sequence
<220> FEATURE:
<223> OTHER INFORMATION: synthetic polynucleotide

<400> SEQUENCE: 47
ccatggctct gtttcaccc                                            19

<210> SEQ ID NO 48
<211> LENGTH: 20
<212> TYPE: DNA
<213> ORGANISM: artificial sequence
<220> FEATURE:
<223> OTHER INFORMATION: synthetic polynucleotide

<400> SEQUENCE: 48
cgagcggcta tacctttacc                                           20

<210> SEQ ID NO 49
<211> LENGTH: 44
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (15)..(16)
<223> OTHER INFORMATION: n is a, c, g, or t

<400> SEQUENCE: 49
gctatacctt taccnnktat tatatgaaat gggtgaaaca gagc                44

<210> SEQ ID NO 50
<211> LENGTH: 44
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (18)..(19)
<223> OTHER INFORMATION: n is a, c, g, or t

<400> SEQUENCE: 50
gctatacctt taccgatnnk tatatgaaat gggtgaaaca gagc                44

<210> SEQ ID NO 51
<211> LENGTH: 44
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (21)..(22)
<223> OTHER INFORMATION: n is a, c, g, or t

<400> SEQUENCE: 51
gctatacctt taccgattat nnkatgaaat gggtgaaaca gagc                44

<210> SEQ ID NO 52
<211> LENGTH: 44

```
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (24)..(25)
<223> OTHER INFORMATION: n is a, c, g, or t

<400> SEQUENCE: 52
gctatacctt taccgattat tatnnkaaat gggtgaaaca gagc         44

<210> SEQ ID NO 53
<211> LENGTH: 44
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (27)..(28)
<223> OTHER INFORMATION: n is a, c, g, or t

<400> SEQUENCE: 53
gctatacctt taccgattat tatatgnnkt gggtgaaaca gagc         44

<210> SEQ ID NO 54
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (48)..(49)
<223> OTHER INFORMATION: n is a, c, g, or t

<400> SEQUENCE: 54
ccttaaattt ctggttataa aaggtttcgc cgttgttcgg attaatmnng ccaatccatt    60
ccagg                                                                65

<210> SEQ ID NO 55
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (45)..(46)
<223> OTHER INFORMATION: n is a, c, g, or t

<400> SEQUENCE: 55
ccttaaattt ctggttataa aaggtttcgc cgttgttcgg attmnnatcg ccaatccatt    60
ccagg                                                                65

<210> SEQ ID NO 56
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (42)..(43)
<223> OTHER INFORMATION: n is a, c, g, or t

<400> SEQUENCE: 56
```

```
ccttaaattt ctggttataa aaggtttcgc cgttgttcgg mnnaatatcg ccaatccatt    60
ccagg                                                                65

<210> SEQ ID NO 57
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (39)..(40)
<223> OTHER INFORMATION: n is a, c, g, or t

<400> SEQUENCE: 57
ccttaaattt ctggttataa aaggtttcgc cgttgttmnn attaatatcg ccaatccatt    60
ccagg                                                                65

<210> SEQ ID NO 58
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (36)..(37)
<223> OTHER INFORMATION: n is a, c, g, or t

<400> SEQUENCE: 58
ccttaaattt ctggttataa aaggtttcgc cgttmnncgg attaatatcg ccaatccatt    60
ccagg                                                                65

<210> SEQ ID NO 59
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (33)..(34)
<223> OTHER INFORMATION: n is a, c, g, or t

<400> SEQUENCE: 59
ccttaaattt ctggttataa aaggtttcgc cmnngttcgg attaatatcg ccaatccatt    60
ccagg                                                                65

<210> SEQ ID NO 60
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (30)..(31)
<223> OTHER INFORMATION: n is a, c, g, or t

<400> SEQUENCE: 60
ccttaaattt ctggttataa aaggtttcmn ngttgttcgg attaatatcg ccaatccatt    60
ccagg                                                                65

<210> SEQ ID NO 61
<211> LENGTH: 65
```

<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (27)..(28)
<223> OTHER INFORMATION: n is a, c, g, or t

<400> SEQUENCE: 61
ccttaaattt ctggttataa aaggtmnngc cgttgttcgg attaatatcg ccaatccatt    60
ccagg                                                               65

<210> SEQ ID NO 62
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (24)..(25)
<223> OTHER INFORMATION: n is a, c, g, or t

<400> SEQUENCE: 62
ccttaaattt ctggttataa aamnnttcgc cgttgttcgg attaatatcg ccaatccatt    60
ccagg                                                               65

<210> SEQ ID NO 63
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (21)..(22)
<223> OTHER INFORMATION: n is a, c, g, or t

<400> SEQUENCE: 63
ccttaaattt ctggttatam nnggtttcgc cgttgttcgg attaatatcg ccaatccatt    60
ccagg                                                               65

<210> SEQ ID NO 64
<211> LENGTH: 26
<212> TYPE: DNA
<213> ORGANISM: artificial sequence
<220> FEATURE:
<223> OTHER INFORMATION: synthetic polynucleotide

<400> SEQUENCE: 64
gggtcgcttt atccttaaat ttctgg                                        26

<210> SEQ ID NO 65
<211> LENGTH: 23
<212> TYPE: DNA
<213> ORGANISM: artificial sequence
<220> FEATURE:
<223> OTHER INFORMATION: synthetic polynucleotide

<400> SEQUENCE: 65
gcaaaagcct ggaatggatt ggc                                           23

<210> SEQ ID NO 66
<211> LENGTH: 65
<212> TYPE: DNA

```
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (17)..(18)
<223> OTHER INFORMATION: n is a, c, g, or t

<400> SEQUENCE: 66
cctggaatgg attggcnnka ttaatccgaa caacggcgaa accttttata accagaaatt      60
taagg                                                                 65

<210> SEQ ID NO 67
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (20)..(21)
<223> OTHER INFORMATION: n is a, c, g, or t

<400> SEQUENCE: 67
cctggaatgg attggcgatn nkaatccgaa caacggcgaa accttttata accagaaatt      60
taagg                                                                 65

<210> SEQ ID NO 68
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (23)..(24)
<223> OTHER INFORMATION: n is a, c, g, or t

<400> SEQUENCE: 68
cctggaatgg attggcgata ttnnkccgaa caacggcgaa accttttata accagaaatt      60
taagg                                                                 65

<210> SEQ ID NO 69
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (26)..(27)
<223> OTHER INFORMATION: n is a, c, g, or t

<400> SEQUENCE: 69
cctggaatgg attggcgata ttaatnnkaa caacggcgaa accttttata accagaaatt      60
taagg                                                                 65

<210> SEQ ID NO 70
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (29)..(30)
<223> OTHER INFORMATION: n is a, c, g, or t
```

<400> SEQUENCE: 70
cctggaatgg attggcgata ttaatccgnn kaacggcgaa accttttata accagaaatt    60
taagg    65

<210> SEQ ID NO 71
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (32)..(33)
<223> OTHER INFORMATION: n is a, c, g, or t

<400> SEQUENCE: 71
cctggaatgg attggcgata ttaatccgaa cnnkggcgaa accttttata accagaaatt    60
taagg    65

<210> SEQ ID NO 72
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (35)..(36)
<223> OTHER INFORMATION: n is a, c, g, or t

<400> SEQUENCE: 72
cctggaatgg attggcgata ttaatccgaa caacnnkgaa accttttata accagaaatt    60
taagg    65

<210> SEQ ID NO 73
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (38)..(39)
<223> OTHER INFORMATION: n is a, c, g, or t

<400> SEQUENCE: 73
cctggaatgg attggcgata ttaatccgaa caacggcnnk accttttata accagaaatt    60
taagg    65

<210> SEQ ID NO 74
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (41)..(42)
<223> OTHER INFORMATION: n is a, c, g, or t

<400> SEQUENCE: 74
cctggaatgg attggcgata ttaatccgaa caacggcgaa nnkttttata accagaaatt    60
taagg    65

<210> SEQ ID NO 75
<211> LENGTH: 65
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (44)..(45)
<223> OTHER INFORMATION: n is a, c, g, or t

<400> SEQUENCE: 75
cctggaatgg attggcgata ttaatccgaa caacggcgaa accnnktata accagaaatt    60
taagg    65

<210> SEQ ID NO 76
<211> LENGTH: 49
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (29)..(30)
<223> OTHER INFORMATION: n is a, c, g, or t

<400> SEQUENCE: 76
ggtaccctgg ccccaataat caaacacmnn ggtcgcgcaa taatacacc    49

<210> SEQ ID NO 77
<211> LENGTH: 49
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (26)..(27)
<223> OTHER INFORMATION: n is a, c, g, or t

<400> SEQUENCE: 77
ggtaccctgg ccccaataat caaamnngcg ggtcgcgcaa taatacacc    49

<210> SEQ ID NO 78
<211> LENGTH: 49
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (23)..(24)
<223> OTHER INFORMATION: n is a, c, g, or t

<400> SEQUENCE: 78
ggtaccctgg ccccaataat cmnncacgcg ggtcgcgcaa taatacacc    49

<210> SEQ ID NO 79
<211> LENGTH: 49
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (20)..(21)
<223> OTHER INFORMATION: n is a, c, g, or t

<400> SEQUENCE: 79
ggtaccctgg ccccaatamn naaacacgcg ggtcgcgcaa taatacacc            49

<210> SEQ ID NO 80
<211> LENGTH: 49
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (17)..(18)
<223> OTHER INFORMATION: n is a, c, g, or t

<400> SEQUENCE: 80
ggtaccctgg ccccamnnat caaacacgcg ggtcgcgcaa taatacacc            49

<210> SEQ ID NO 81
<211> LENGTH: 21
<212> TYPE: DNA
<213> ORGANISM: artificial sequence
<220> FEATURE:
<223> OTHER INFORMATION: synthetic polynucleotide

<400> SEQUENCE: 81
cggtcagggt ggtaccctgg c                                         21

<210> SEQ ID NO 82
<211> LENGTH: 20
<212> TYPE: DNA
<213> ORGANISM: artificial sequence
<220> FEATURE:
<223> OTHER INFORMATION: synthetic polynucleotide

<400> SEQUENCE: 82
cggtgtatta ttgcgcgacc                                           20

<210> SEQ ID NO 83
<211> LENGTH: 49
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (20)..(21)
<223> OTHER INFORMATION: n is a, c, g, or t

<400> SEQUENCE: 83
ggtgtattat tgcgcgaccn nkgtgtttga ttattggggc cagggtacc            49

<210> SEQ ID NO 84
<211> LENGTH: 49
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (23)..(24)
<223> OTHER INFORMATION: n is a, c, g, or t

<400> SEQUENCE: 84
ggtgtattat tgcgcgaccc gcnnktttga ttattggggc cagggtacc            49

<210> SEQ ID NO 85
<211> LENGTH: 49
<212> TYPE: DNA

```
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (26)..(27)
<223> OTHER INFORMATION: n is a, c, g, or t

<400> SEQUENCE: 85
ggtgtattat tgcgcgaccc gcgtgnnkga ttattggggc cagggtacc            49

<210> SEQ ID NO 86
<211> LENGTH: 49
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (29)..(30)
<223> OTHER INFORMATION: n is a, c, g, or t

<400> SEQUENCE: 86
ggtgtattat tgcgcgaccc gcgtgtttnn ktattggggc cagggtacc            49

<210> SEQ ID NO 87
<211> LENGTH: 49
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (32)..(33)
<223> OTHER INFORMATION: n is a, c, g, or t

<400> SEQUENCE: 87
ggtgtattat tgcgcgaccc gcgtgtttga tnnktggggc cagggtacc            49

<210> SEQ ID NO 88
<211> LENGTH: 36
<212> TYPE: DNA
<213> ORGANISM: artificial sequence
<220> FEATURE:
<223> OTHER INFORMATION: synthetic polynucleotide

<400> SEQUENCE: 88
ggaaagcctc tgaggaccag cacggatgcc ctgtgc                         36

<210> SEQ ID NO 89
<211> LENGTH: 44
<212> TYPE: DNA
<213> ORGANISM: artificial sequence
<220> FEATURE:
<223> OTHER INFORMATION: synthetic polynucleotide

<400> SEQUENCE: 89
cgaaattaat acgactcact atagggagac cacaacggtt tccc                44

<210> SEQ ID NO 90
<211> LENGTH: 47
<212> TYPE: DNA
<213> ORGANISM: artificial sequence
<220> FEATURE:
<223> OTHER INFORMATION: synthetic polynucleotide

<400> SEQUENCE: 90 aaccccgca taggctgggg gttggaaagc ctctgaggac cagcacg              47
```

<210> SEQ ID NO 91
<211> LENGTH: 191
<212> TYPE: DNA
<213> ORGANISM: artificial sequence
<220> FEATURE:
<223> OTHER INFORMATION: synthetic polynucleotide

<400> SEQUENCE: 91
gggagaccac aacggtttcc ctctagaaat aattttgttt aactttaaga aggagatata    60
catatggaag tgcagctgca gcagagcggc ccggaactgg tgaaaccggg cgcgagcgtg   120
aaaatgagct gcaaagcgag cggctatacc tttaccgatt attatatgaa atgggtgaaa   180
cagagccatg g                                                        191

<210> SEQ ID NO 92
<211> LENGTH: 138
<212> TYPE: DNA
<213> ORGANISM: artificial sequence
<220> FEATURE:
<223> OTHER INFORMATION: synthetic polynucleotide

<400> SEQUENCE: 92
cgagcggcta ccctttacc gattattata tgaaatgggt gaaacagagc catggcaaaa     60
gcctggaatg gattggcgat attaatccga acaacggcga aaccttttat aaccagaaat   120
ttaaggataa agcgaccc                                                 138

<210> SEQ ID NO 93
<211> LENGTH: 210
<212> TYPE: DNA
<213> ORGANISM: artificial sequence
<220> FEATURE:
<223> OTHER INFORMATION: synthetic polynucleotide

<400> SEQUENCE: 93
gcaaaagcct ggaatggatt ggcgatatta atccgaacaa cggcgaaacc ttttataacc    60
agaaatttaa ggataaagcg accctgaccg tggataaaag cagcagcacc gcgtatatgc   120
agctgaacag cctgaccagc gaagatagcg cggtgtatta ttgcgcgacc cgcgtgtttg   180
attattgggg ccagggtacc accctgaccg                                    210

<210> SEQ ID NO 94
<211> LENGTH: 512
<212> TYPE: DNA
<213> ORGANISM: artificial sequence
<220> FEATURE:
<223> OTHER INFORMATION: synthetic polynucleotide

<400> SEQUENCE: 94
cggtgtatta ttgcgcgacc cgcgtgtttg attattgggg ccagggtacc accctgaccg    60
tgagcagcgc gaaaaccacc ccgccgagcg tgtatccgct ggcgccgggc agcgcggcgc   120
agaccaacag catggtgacc ctgggctgcc tggtgaaagg ctattttccg gaaccggtga   180
ccgtgacctg gaacagcggc agcctgagca gcggcgtgca tacctttccg gcggtgctgc   240
agagcgatct gtataccctg agcagcagcg tgaccgtgcc gagcagcacc tggccgagcg   300
aaaccgtgac ctgcaacgtg gcgcatccgg cgagcagcac caaagtggat aaaaaaattg   360
gagctggtgc aggctctggt gctggcgcag gttctccagc agcggtgccg gcagcagttc   420
ctgctgcggt gggcgaaggc gagggagagt tcagtacgcc agtttggatc tcgcaggcac   480

```
agggcatccg tgctggtcct cagaggcttt cc                                  512

<210> SEQ ID NO 95
<211> LENGTH: 43
<212> TYPE: DNA
<213> ORGANISM: artificial sequence
<220> FEATURE:
<223> OTHER INFORMATION: synthetic polynucleotide

<400> SEQUENCE: 95
gctacaaacg cgtacgctat ggaagtgcag ctgcagcaga gcg                      43
```

ANTI-TROPONIN T ANTIBODIES

CROSS-REFERENCE TO RELATED APPLICATION

The present invention claims priority to International Patent Application No. PCT/EP2019/056069 (published as WO2019/175127), filed Mar. 12, 2019, which claims priority to EP Patent Application No. 18161697.0, filed Mar. 14, 2018, both of which are hereby incorporated by reference in their entireties.

SEQUENCE LISTING

This application incorporates by reference the material in the .txt file titled 17015662_1_1, which was created on Sep. 9, 2020 and is 49058 bytes.

The present invention relates to a novel monoclonal antibody that specifically binds to cardiac troponin T (SEQ ID NO:1) the antibody being characterized in that the CDRs comprise the following amino acid sequences or a variant thereof that differs in at most one amino acid substitution (i) in the light chain variable domain a CDR1 comprising the amino acid sequence of SEQ ID NO:2, a CDR2 comprising the amino acid sequence of SEQ ID NO:3, and a CDR3 comprising the amino acid sequence of SEQ ID NO:4, and (ii) in the heavy chain variable domain a CDR1 comprising the amino acid sequence of SEQ ID NO:5; SEQ ID NO:6; or of SEQ ID NO:7, a CDR2 comprising the amino acid sequence of SEQ ID NO:8, or of SEQ ID NO:9, and a CDR3 comprising the amino acid sequence of SEQ ID NO:10; of SEQ ID NO:11; of SEQ ID NO:12; or of SEQ ID NO:13, wherein at least two of the CDRs are selected from a CDR1 of SEQ ID NO:6 or SEQ ID NO:7, a CDR2 of SEQ ID NO:9, and a CDR3 of SEQ ID NO:12, or wherein the CDR1 is of SEQ ID NO:7, the CDR2 is of SEQ ID NO:8, and the CDR3 is of SEQ ID NO:11 or of SEQ ID NO:13, with the proviso that in case a CDR1 of SEQ ID NO:6 is present then either a) the CDR3 is neither SEQ ID NO:11 nor SEQ ID NO:13 or b) the CDR2 and the CDR3 within this antibody are not at the same time of SEQ ID NO:8 and SEQ ID NO:12, respectively.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Cardiac troponins are sensitive and specific biomarkers of cardiac injury. In particular, cardiac troponin T (cTnT) is highly cardiac specific, and it is not present in serum following non-myocardial muscle or other tissue damage. In addition, cTnT has been shown to be a more persistent and sensitive biomarker than others used for diagnosing myocardial infarction. Thus cardiac troponins generally are generally useful for diagnosing acute myocardial ischemia, and cTnT is especially useful.

Cardiac troponin T is a widely used biomarker in patients with cardiac disease. Its utility in patients with cardiac diseases has recently been reviewed by Westermann et al. (Nature Reviews/Cardiology, vol 14 (2017) 473-483. The use of cTnT is well established in patients with suspected acute myocardial infarction (AMI), but troponin measurement is also used in other acute and nonacute settings. In patients with suspected AMI, early decision-making is crucial to allow rapid treatment and further diagnostic evaluation.

Newer, high-sensitivity assays for troponin enable the detection of distinctly lower concentrations. Using these assays and very low cut-off concentrations, several rapid diagnostic strategies have been reported to improve diagnosis in acute cardiac care. Furthermore, noncoronary and nonacute applications of troponin assays—for example as a biomarker in patients with heart failure, pulmonary embolism, or stable coronary artery disease—are on the horizon and might improve individual risk stratification.

Cardiac troponin T is usually measured in a sandwich type immuno assay, wherein at least one antibody is used to capture cTnT and at least second (labeled) antibody is used to detect cTnT in a sample. This is also the case in fifth generation assay for cTnT sold by Roche Diagnostics, Germany. The monoclonal antibody 12.1A11.11-7, produced by hybridoma clone 7.1 A 12.2-22 (ECACC 89060901) as deposited with European Collection of Animal Cell Cultures, GB, has been used since almost three decades as the best detection antibody in assays for cTnT. Ever since this antibody has been generated in 1989, no better monoclonal antibody for detection of cTnT has surfaced.

Over the past several years ever more sensitive assays for measurement of the various troponins have been developed, e.g. based on sophisticated techniques for labeling of detection antibodies used in such assays.

Many studies have evaluated the various high-sensitivity assays for troponin both for their potential to improve the triaging of patients with suspected AMI as well as their utility in other fields of clinical diagnosis.

Even the most sensitive troponin assays have been reported to fail to measure troponin in a certain percentage of healthy individuals (see e.g. Westermann et al., above). Obviously, assay sensitivity, is of utmost importance e.g. in the detection of cTnT and improvement to that end would be highly desirable.

This need is addressed by the present invention by providing the embodiments as defined in the claims.

It has now quite surprisingly been found that certain mutations can be introduced into the complementarity determining regions (CDRs) of antibody 12.1A11.11-7 which on the one hand do not negatively influence the complex formation of the antibody with cTnT but represent a significant improvement with respect to the stability of the complex formed between cTnT and such mutant antibodies. Via these surprising properties an assay for cTnT with superior sensitivity is feasible.

Accordingly, the present invention relates to a novel monoclonal antibody that specifically binds to cardiac troponin T (SEQ ID NO:1) the antibody being characterized in that the CDRs comprise the following amino acid sequences or a variant thereof that differs in at most one amino acid substitution (i) in the light chain variable domain a CDR1 comprising the amino acid sequence of SEQ ID NO:2, a CDR2 comprising the amino acid sequence of SEQ ID NO:3, and a CDR3 comprising the amino acid sequence of SEQ ID NO:4, and (ii) in the heavy chain variable domain a CDR1 comprising the amino acid sequence of SEQ ID NO:5; SEQ ID NO:6; or of SEQ ID NO:7, a CDR2 comprising the amino acid sequence of SEQ ID NO:8, or of SEQ ID NO:9, and a CDR3 comprising the amino acid sequence of SEQ ID NO:10; of SEQ ID NO:11; of SEQ ID NO:12; or of SEQ ID NO:13, wherein at least two of the CDRs are selected from a CDR1 of SEQ ID NO:6 or SEQ ID NO:7, a CDR2 of SEQ ID NO:9 and a CDR3 of SEQ ID NO:12, or wherein the CDR1 is of SEQ ID NO:7, the CDR2 is of SEQ ID NO:8 and the CDR3 is of SEQ ID NO:11 or of SEQ ID NO:13, with the proviso that in case a CDR1 of SEQ ID NO:6 is present then either a) the CDR3 is neither SEQ ID NO:11 nor SEQ ID NO:13 or b) the CDR2 and the CDR3 within this antibody are not at the same time of SEQ ID NO:8 and SEQ ID NO:12, respectively.

The antibody of the present invention can also be described as a novel monoclonal antibody that specifically binds to cardiac troponin T (SEQ ID NO:1) the antibody being characterized in that the CDRs comprise the following amino acid sequences or a variant thereof that differs in at most one amino acid substitution
  (a) in the light chain variable domain a CDR1 comprising the amino acid sequence of SEQ ID NO:2, a CDR2 comprising the amino acid sequence of SEQ ID NO:3, and a CDR3 comprising the amino acid sequence of SEQ ID NO:4, and
  (b) in the heavy chain variable domain a set of CDRs selected from:
    (i) a CDR1 of SEQ ID NO:6, a CDR2 of SEQ ID NO:9 and a CDR3 of SEQ ID NO:12, (ii) a CDR1 of SEQ ID NO:7; a CDR2 of SEQ ID NO:8 and a CDR3 of SEQ ID NO:11,
    (iii) a CDR1 of SEQ ID NO:7, a CDR2 of SEQ ID NO:8 and a CDR3 of SEQ ID NO:13,
    (iv) a CDR1 of SEQ ID NO:7, a CDR2 of SEQ ID NO:9 and a CDR3 of SEQ ID NO:13,
    (v) a CDR1 of SEQ ID NO:6, a CDR2 of SEQ ID NO:9 and a CDR3 of SEQ ID NO:10,
    (vi) a CDR1 of SEQ ID NO:7, a CDR2 of SEQ ID NO:9 and a CDR3 of SEQ ID NO:11,
    (vii) a CDR1 of SEQ ID NO:7, a CDR2 of SEQ ID NO:9 and a CDR3 of SEQ ID NO:12,
    (viii) a CDR1 of SEQ ID NO:7, a CDR2 of SEQ ID NO:9 and a CDR3 of SEQ ID NO:10,
    (ix) a CDR1 of SEQ ID NO:7, a CDR2 of SEQ ID NO:8 and a CDR3 of SEQ ID NO:12, or
    (x) a CDR1 of SEQ ID NO:5, a CDR2 of SEQ ID NO:9 and a CDR3 of SEQ ID NO:12.

The definition (i) to (x) given above for the CDRs comprised in the heavy chain variable domain represents an alternative description of the heavy chain CDRs according to the present disclosure. This definition can be used to describe and define the heavy chain variable domain in all the various embodiments relating to the heavy chain variable domain given in the present disclosure.

The overall structure of antibodies is well known in the art and comprises of two heavy chains and two light chains, connected by disulfide bonds. The heavy chains and the light chains each consist of one constant domain and one variable domain. Binding specificity to an antigen is provided by the variable domains of the light and heavy chains that form the antibody. More specifically, the parts of antibodies that determine their specificity and make contact with a specific ligand are referred to as the complementarity determining regions (CDRs). The CDRs are the most variable part of the molecule and contribute to the diversity of these molecules. There are three CDR regions CDR1, CDR2 and CDR3 in each variable domain, embedded into four framework regions (FWs). As used herein, CDR-HC (or CDR(HC)) depicts a CDR region of a variable heavy chain and CDR-LC (or CDR(LC)) relates to a CDR region of a variable light chain. Similarly, FW-HC (or FW(HC)) depicts a framework region of a variable heavy chain and FW-LC (or FW(LC)) relates to a framework region of a variable light chain.

The term "comprising", as used in accordance with the present invention, denotes that further sequences/components can be included in addition to the specifically recited sequences and/or components. However, this term also encompasses that the claimed subject-matter consists of exactly the recited sequences and/or components.

In those embodiments where the antibody of the invention includes more than the recited amino acid sequence, additional amino acids can be present at either the N-terminal end, or the C-terminal end, or both. Additional sequences can include e.g. sequences introduced e.g. for purification or detection, as discussed in detail herein below. Furthermore, where individual sequences "comprise" the recited sequence, they also can include additional amino acids at either the N-terminal end, or the C-terminal end, or both.

In accordance with the present invention, the antibody specifically binds to human cardiac troponin T (cTnT) of SEQ ID NO:1. It will be appreciated that also in the cases where the antibody of the invention comprises additional amino acids, as detailed above, said antibody necessarily has to specifically bind to cTnT.

The term "specifically binds" (also referred to herein as "specifically interacts"), in accordance with the present invention, means that the antibody specifically binds only cTnT, but does not or essentially does not cross-react with a different protein, in particular a different protein of similar structure such as e.g. troponin I (SEQ ID NO:33).

Corresponding methods for analyzing the specificity of an antibody are described e.g. in Harlow & Lane (1988) Antibodies: A Laboratory Manual, Cold Spring Harbor Laboratory Press, and in Harlow & Lane (1999) Using Antibodies: A Laboratory Manual, Cold Spring Harbor Laboratory Press. Non-limiting examples of suitable studies are e.g. binding studies, blocking and competition studies with structurally and/or functionally closely related molecules. These studies can be carried out by methods such as e.g. FACS analysis, flow cytometric titration analysis (FACS titration), surface plasmon resonance (SPR, e.g. with BIAcore®), isothermal titration calorimetry (ITC), fluorescence titration, or by radiolabeled ligand binding assays. Further methods include e.g. Western Blots, ELISA (including competition ELISA)-, RIA-, ECL-, and IRMA-tests.

In context of the present invention, the term "antibody" relates to full immunoglobulin molecules as well as to antigen binding fragments thereof, like, Fab, Fab', F(ab')$_2$, Fv. Furthermore, the term relates to modified and/or altered antibody molecules, as well as to recombinantly or synthetically generated/synthesized antibodies. The term "antibody" also comprises bifunctional antibodies, trifunctional antibodies, fully-human antibodies, chimeric antibodies, and antibody constructs, like single chain Fvs (scFv) or antibody-fusion proteins.

A "Fab fragment" as used herein is comprised of one light chain and the $C_H1$ and variable regions of one heavy chain. The heavy chain of a Fab molecule cannot form a disulfide bond with another heavy chain molecule. A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule. A "F(ab')$_2$ fragment" contains two light chains and two heavy chains containing a portion of the constant region between the $C_H1$ and $C_H2$ domains, such that an interchain disulfide bond is formed between the two heavy chains A F(ab')$_2$ fragment thus is composed of two Fab' fragments that are held together by a disulfide bond between the two heavy chains.

Fab/c fragment contain both Fc and Fab determinants, wherein an "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

The "Fv region" comprises the variable regions from both the heavy and light chains, but lacks the constant regions. "Single-chain Fvs" (also abbreviated as "scFv") are antibody fragments that have, in the context of the present invention, the $V_H$ and $V_L$ domains of an antibody, wherein these domains are present in a single polypeptide chain. Generally, the scFv polypeptide further comprises a polypeptide linker between the $V_H$ and $V_L$ domains which enables the scFv to form the desired structure for antigen binding. Techniques described for the production of single chain antibodies are described, e.g., in Plückthun in The Pharmacology of Monoclonal Antibodies, Rosenburg and Moore eds. Springer-Verlag, N.Y. 113 (1994), 269-315.

The term "fully-human antibody" as used herein refers to an antibody which comprises human immunoglobulin protein sequences only. Nonetheless, a fully human antibody may contain murine carbohydrate chains if produced in a mouse, in a mouse cell or in a hybridoma derived from a mouse cell or it may contain rat carbohydrate chains if produced in a rat, in a rat cell, or in a hybridoma derived from a rat cell. Similarly, a fully human antibody may contain hamster carbohydrate chains if produced in a hamster, in a hamster cell, such as e.g. CHO cells, or in a hybridoma derived from a hamster cell. On the other hand, a "mouse antibody" or "murine antibody" is an antibody that comprises mouse (murine) immunoglobulin protein sequences only, while a "rat antibody" or a "rabbit antibody" is an antibody that comprises rat or rabbit immunoglobulin sequences, respectively, only. As with fully human antibodies, such murine, rat or rabbit antibodies may contain carbohydrate chains from other species, if produced in such an animal or a cell of such an animal. For example, the antibodies may contain hamster carbohydrate chains if produced in a hamster cell, such as e.g. CHO cells, or in a hybridoma derived from a hamster cell. Fully-human antibodies can be produced, for example, by phage display which is a widely used screening technology which enables production and screening of fully human antibodies. Also phage antibodies can be used in context of this invention. Phage display methods are described, for example, in U.S. Pat. Nos. 5,403,484, 5,969,108 and 5,885,793. Another technology which enables development of fully-human antibodies involves a modification of mouse hybridoma technology. Mice are made transgenic to contain the human immunoglobulin locus in exchange for their own mouse genes (see, for example, U.S. Pat. No. 5,877,397).

The term "chimeric antibodies" refers to antibodies that comprise a variable region of a human or non-human species fused or chimerized to an antibody region (e.g., constant region) from another species, either human or non-human (e.g., mouse, horse, rabbit, dog, cow, chicken).

As mentioned above, the term "antibody" also encompasses antibody constructs, such as antibody-fusion proteins, wherein the antibody comprises (an) additional domain(s), e.g. for the isolation and/or preparation of recombinantly produced constructs, in addition to the domains defined herein by specific amino acid sequences.

The antibody of the present invention can be produced such that it is a recombinant antibody, for example a recombinant human antibody, or a hetero-hybrid antibody, yet comprising the CDRs as disclosed and defined in the present invention.

The term "recombinant antibody" includes all antibodies that are prepared, expressed, created or isolated by recombinant means, such as antibodies isolated from an animal (e.g., a mouse) that is transgenic for human immunoglobulin genes, antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "hetero-hybrid antibody" refers to an antibody having light and heavy chains that originate from different organisms. For example, an antibody having a human heavy chain associated with a murine light chain is a hetero-hybrid antibody. Examples of hetero-hybrid antibodies include chimeric and humanized antibodies.

The antibody in accordance with the present invention comprises the recited combinations of light chain CRDs and heavy chain CRDs. The surrounding framework sequence of the respective variable domain into which the CDRs are incorporated can be chosen by the skilled person without further ado. For example, the framework sequences described further below or the specific framework sequence employed in the appended examples can be used.

In accordance with the present invention, the CDRs can comprise the specifically recited sequence or can differ therefrom in at most one amino acid substitution. As such, one amino acid in each of the CDRs can be replaced by a different amino acid. It will be appreciated that also encompassed is that an amino acid substitution is present in some, but not all CDRs of one chain or of one antibody.

The term "substitution", in accordance with the present invention, refers to the replacement of an amino acid with another amino acid. Thus, the total number of amino acids remains the same. The deletion of an amino acid at a certain position and the introduction of one (or more) amino acid(s) at a different position is explicitly not encompassed by the term "substitution". Substitutions, in accordance with the present invention, can be conservative amino acid substitutions or non-conservative amino acid substitutions. The term "conservative amino acid substitution" is well known in the art and refers to the replacement of an amino acid with a different amino acid having similar structural and/or chemical properties. Such similarities include e.g. a similarity in polarity, charge, solubility, hydrophobicity, hydrophilicity, and/or the amphipathic nature of the residues involved. The amino acid substitution is a conservative amino acid substitutions, in case one amino acid of one of the following groups is substituted by another amino acid of the same group: nonpolar (hydrophobic) amino acids include alanine, valine, leucine, isoleucine, proline, phenylalanine, tyrosine, tryptophan, and methionine; polar neutral amino acids include glycine, serine, threonine, cysteine, asparagine, and glutamine; positively charged (basic) amino acids include arginine, lysine, and histidine; and negatively charged (acidic) amino acids include aspartic acid and glutamic acid. In one embodiment, the substitution in any (or all) of the CDRs is a conservative amino acid substitution. It will be appreciated that also an antibody having such substituted amino acids in one or more of the CDRs necessarily has to be an antibody that specifically binds to cTnT of SEQ ID NO:1.

In one embodiment, the antibody that specifically binds to human cardiac troponin T (SEQ ID NO:1) is an antibody being characterized in that (i) the CDR in the light chain variable domain comprises a CDR1 comprising the amino acid sequence of SEQ ID NO:2, a CDR2 comprising the amino acid sequence of SEQ ID NO:3, and a CDR3 comprising the amino acid sequence of SEQ ID NO:4, or a variant thereof that differs in at most one amino acid substitution per CDR and (ii) the CDR in the heavy chain variable domain comprises a CDR1 comprising the amino acid sequence of SEQ ID NO:5; SEQ ID NO:6; or of SEQ ID NO:7, a CDR2 comprising the amino acid sequence of SEQ ID NO:8; or of SEQ ID NO:9, and a CDR3 comprising the amino acid sequence of SEQ ID NO:10; of SEQ ID NO:11; of SEQ ID NO:12; or of SEQ ID NO:13, wherein at least two of the CDRs are selected from a CDR1 of SEQ ID NO:6; or SEQ ID NO:7, a CDR2 of SEQ ID NO:9 and a CDR3 of SEQ ID NO:12, or wherein the CDR1 is of SEQ ID NO:7, the CDR2 is of SEQ ID NO:8 and the CDR3 is of SEQ ID NO:11 or of SEQ ID NO:13, with the proviso that in case a CDR1 of SEQ ID NO:6 is present then either a) the CDR3 is neither SEQ ID NO:11 nor SEQ ID NO:13 or b) the CDR2 and the CDR3 within this antibody are not at the same time of SEQ ID NO:8 and SEQ ID NO:12, respectively.

In one embodiment the present invention discloses an antibody that specifically binds to human cardiac troponin T (SEQ ID NO:1) the antibody being characterized in that the CDRs comprise the following amino acid sequences (i) in the light chain variable domain a CDR1 comprising the amino acid sequence of SEQ ID NO:2, a CDR2 comprising the amino acid sequence of SEQ ID NO:3, and a CDR3 comprising the amino acid sequence of SEQ ID NO:4, and (ii) in the heavy chain variable domain a CDR1 comprising the amino acid sequence of SEQ ID NO:5; SEQ ID NO:6; or of SEQ ID NO:7, a CDR2 comprising the amino acid sequence of SEQ ID NO:8; or of SEQ ID NO:9, and a CDR3 comprising the amino acid sequence of SEQ ID NO:10; of SEQ ID NO:11; of SEQ ID NO:12; or of SEQ ID NO:13, wherein at least two of the CDRs are selected from a CDR1 of SEQ ID NO:6 or SEQ ID NO:7, a CDR2 of SEQ ID NO:9, and a CDR3 of SEQ ID NO:12, or wherein the CDR1 is of SEQ ID NO:7, the CDR2 is of SEQ ID NO:8, and the CDR3 is of SEQ ID NO:11 or of SEQ ID NO:13, with the proviso that in case a CDR1 of SEQ ID NO:6 is present then either a) the CDR3 is neither SEQ ID NO:11 nor SEQ ID NO:13 or b) the CDR2 and the CDR3 within this antibody are not at the same time of SEQ ID NO:8 and SEQ ID NO:12, respectively.

Furthermore, the present invention also relates to an antibody that specifically binds to human cardiac troponin T (SEQ ID NO:1),
wherein the antibody comprises a light chain variable domain consisting of framework regions (FW) and CDRs as represented in formula I:

FW(LC)1-CDR(LC)1-FW(LC)2-CDR(LC)2-FW(LC)
3-CDR(LC)3-FW(LC)4     (formula I)

and a heavy chain variable domain consisting of FWs and CDRs as represented in formula II:

FW(HC)1-CDR(HC)1-FW(HC)2-CDR(HC)2-FW
(HC)3-CDR(HC)3-FW(HC)4     (formula II), wherein the FWs comprise the following amino acid sequences or a variant thereof that is at least 85% identical thereto:
in the light chain
FW(LC)1 the amino acid sequence of SEQ ID NO:14;
FW(LC)2 the amino acid sequence of SEQ ID NO:15;
FW(LC)3 the amino acid sequence of SEQ ID NO:16;
FW(LC)4 the amino acid sequence of SEQ ID NO:17;
and in the heavy chain
FW(HC)1 the amino acid sequence of SEQ ID NO:18;
FW(HC)2 the amino acid sequence of SEQ ID NO:19;
FW(HC)3 the amino acid sequence of SEQ ID NO:20;
FW(HC)4 the amino acid sequence of SEQ ID NO:21;
and wherein the CDRs comprise the following amino acid sequences (i) in the light chain variable domain a CDR1 comprising the amino acid sequence of SEQ ID NO:2, a CDR2 comprising the amino acid sequence of SEQ ID NO:3, and a CDR3 comprising the amino acid sequence of SEQ ID NO:4, and (ii) in the heavy chain variable domain a CDR1 comprising the amino acid sequence of SEQ ID NO:5; SEQ ID NO:6; or of SEQ ID NO:7, a CDR2 comprising the amino acid sequence of SEQ ID NO:8; or of SEQ ID NO:9, and a CDR3 comprising the amino acid sequence of SEQ ID NO:10; of SEQ ID NO:11; of SEQ ID NO:12; or of SEQ ID NO:13, wherein at least two of the CDRs are selected from a CDR1 of SEQ ID NO:6 or SEQ ID NO:7, a CDR2 of SEQ ID NO:9, and a CDR3 of SEQ ID NO:12, or wherein the CDR1 is of SEQ ID NO:7, the CDR2 is of SEQ ID NO:8, and the CDR3 is of SEQ ID NO:11 or of SEQ ID NO:13, with the proviso that in case a CDR1 of SEQ ID NO:6 is present then either a) the CDR3 is neither SEQ ID NO:11 nor SEQ ID NO:13 or b) the CDR2 and the CDR3 within this antibody are not at the same time of SEQ ID NO:8 and SEQ ID NO:12, respectively, or a variant of these CDR that differs in at most one amino acid substitution per CDR.

Furthermore the present invention discloses an anti-cTnT antibody comprising a light chain variable domain consisting of framework regions (FW) and CDRs as represented in formula I:

FW(LC)1-CDR(LC)1-FW(LC)2-CDR(LC)2-FW(LC)
3-CDR(LC)3-FW(LC)4     (formula I)

and a heavy chain variable domain consisting of FWs and CDRs as represented in formula II:

FW(HC)1-CDR(HC)1-FW(HC)2-CDR(HC)2-FW
(HC)3-CDR(HC)3-FW(HC)4     (formula II), wherein the FWs comprise the following amino acid sequences or a variant thereof that is at least 85% identical thereto:
in the light chain
FW(LC)1 the amino acid sequence of SEQ ID NO:14;
FW(LC)2 the amino acid sequence of SEQ ID NO:15;
FW(LC)3 the amino acid sequence of SEQ ID NO:16;
FW(LC)4 the amino acid sequence of SEQ ID NO:17;
and in the heavy chain
FW(HC)1 the amino acid sequence of SEQ ID NO:18;
FW(HC)2 the amino acid sequence of SEQ ID NO:19;
FW(HC)3 the amino acid sequence of SEQ ID NO:20;
FW(HC)4 the amino acid sequence of SEQ ID NO:21;

and wherein the CDRs comprise the following amino acid sequences (i) in the light chain variable domain a CDR1 comprising the amino acid sequence of SEQ ID NO:2, a CDR2 comprising the amino acid sequence of SEQ ID NO:3, and a CDR3 comprising the amino acid sequence of SEQ ID NO:4, and (ii) in the heavy chain variable domain a CDR1 comprising the amino acid sequence of SEQ ID NO:5; SEQ ID NO:6; or of SEQ ID NO:7, a CDR2 comprising the amino acid sequence of SEQ ID NO:8; or of SEQ ID NO:9, and a CDR3 comprising the amino acid sequence of SEQ ID NO:10; of SEQ ID NO:11; of SEQ ID NO:12; or of SEQ ID NO:13, wherein at least two of the CDRs are selected from a CDR1 of SEQ ID NO:6 or SEQ ID NO:7, a CDR2 of SEQ ID NO:9, and a CDR3 of SEQ ID NO:12, or wherein the CDR1 is of SEQ ID NO:7, the CDR2 is of SEQ ID NO:8, and the CDR3 is of SEQ ID NO:11 or of SEQ ID NO:13, with the proviso that in case a CDR1 of SEQ ID NO:6 is present then either a) the CDR3 is neither SEQ ID NO:11 nor SEQ ID NO:13 or b) the CDR2 and the CDR3 within this antibody are not at the same time of SEQ ID NO:8 and SEQ ID NO:12, respectively.

The primary structure shown in formula I represents the order of the components of the light chain variable domain of the antibody of the present invention from the N-terminus to the C-terminus. The primary structure shown in formula II represents the order of the components of the heavy chain variable domain of the antibody of the present invention from the N-terminus to the C-terminus. In each case, framework region (FW) 1 represents the most N-terminal part of the respective variable chain domain, while FW 4 represents the most C-terminal part of the respective variable chain domain.

As defined above, the respective FW and CDR sequences "comprise" the recited amino acid sequences. In one embodiment the respective FW and CDR sequences consist of said amino acid sequences, i.e. the light chain variable domain(s) and heavy chain variable domain(s) of the anti-troponin T antibody of the invention consist of the FWs and CDRs as represented in formula I and formula II, respectively, wherein the respective FW and CDR sequences consist of the recited amino acid sequences.

With regard to the CDRs and variants thereof, the above provided definitions and specifically exemplified embodiments apply mutatis mutandis.

With regard to the framework regions, a certain degree of variability is also envisaged herein, i.e. the individual FWs can comprise the, or consist of the specifically recited amino acid sequence or of an amino acid sequence at least 85% identical thereto. Preferably, the identity is at least 90%, more preferred at least 92.5%, more preferred at least 95%, even more preferred the identity is at least 98%, such as at least 99% and most preferably the identity is at least 99.5%. It will be appreciated that for different FWs, a different degree of sequence identity may be allowable, depending on the actual sequence and e.g. the length of the respective FW sequence, as well as its location within the respective variable chain domain.

In accordance with the present invention, the term "% sequence identity" describes the number of matches ("hits") of identical amino acids of two or more aligned amino acid sequences as compared to the number of amino acid residues making up the overall length of the amino acid sequences (or the overall compared part thereof). Percent identity is determined by dividing the number of identical residues by the total number of residues and multiplying the product by 100.

In other terms, using an alignment, the percentage of amino acid residues that are the same (e.g., 85% identity) may be determined for two or more sequences or sub-sequences when these (sub)sequences are compared and aligned for maximum correspondence over a window of comparison, or over a designated region as measured using a sequence comparison algorithm as known in the art, or when manually aligned and visually inspected.

Those having skill in the art know how to determine percent sequence identity between/among sequences using, for example, algorithms such as those based on the NCBI BLAST algorithm (Altschul, S. F. et al. [1997] Nucleic Acids Res. 25:3389-3402), CLUSTALW computer program (Tompson, J. D. et al. [1994] Nucleic Acids Res. 22:4673-4680) or FASTA (Pearson, W. R. & Lipman, D. J. [1988] Proc. Natl. Acad. Sci. U.S.A. 85:2444-2448). In one embodiment, the NCBI BLAST algorithm is employed in accordance with this invention. For amino acid sequences, the BLASTP program uses as default a word length (W) of 3, and an expectation (E) of 10. The BLOSUM62 scoring matrix (Henikoff, S. & Henikoff, J. G. [1992] Proc. Natl. Acad. Sci. U.S.A. 89:10915-10919) uses alignments (B) of 50, expectation (E) of 10, M=5, N=4, and a comparison of both strands. Accordingly, in those embodiments where a % sequence identity is indicated, all the amino acid sequences having a sequence identity of at least 85% as determined with the NCBI BLAST program fall under the scope of said embodiments.

The above described degree of variation in the framework regions as compared to the respective specifically recited amino acid sequence can be due to the substitution, insertion, addition, or deletion of (an) amino acid(s).

The term "substitution", has been defined herein above. In those cases where more than one amino acid is to be substituted, each amino acid is independently replaced with another amino acid, i.e. for each amino acid that is removed a different amino acid is introduced at the same position.

The term "insertion", in accordance with the present invention, refers to the addition of one or more amino acids to the specifically recited amino acid sequence, wherein the addition is not to the N- or C-terminal end of the polypeptide.

The term "addition", in accordance with the present invention, refers to the addition of one or more amino acids to the specifically recited amino acid sequence, either to the N- or C-terminal end of the polypeptide, or to both.

The term "deletion", as used in accordance with the present invention, refers to the loss of one or more amino acids from the specifically recited amino acid sequence.

In one embodiment, the variation in the amino acid sequences of the framework regions is due to the substitution of (an) amino acid(s). Substitutions, as defined herein above, can be conservative amino acid substitutions or non-conservative amino acid substitutions. The definitions and specifically exemplified embodiments provided above with regard to the term "substitution" apply mutatis mutandis. In one embodiment, the substitutions in the framework regions are conservative amino acid substitutions.

In a further embodiment, the CDRs consist of the above recited specific sequences (i.e. without any variations) and the above recited framework regions (FWs) comprise at most the following amount of amino acid variations within the above recited specific sequences:

FW(LC)1 at most 3 amino acid variations;
FW(LC)2 at most 2 amino acid variations;
FW(LC)3 at most 4 amino acid variations;
FW(LC)4 at most 1 amino acid variation; and FW(HC)1 at most 3 amino acid variations;
FW(HC)2 at most 2 amino acid variations;
FW(HC)3 at most 4 amino acid variations; and
FW(HC)4 at most 1 amino acid variation.

In a further embodiment, the amino acid variations in the FWs are substitutions.

In a further embodiment, the total amount of variations present in the light or heavy chain variable domain framework regions is at most 9 amino acid substitutions, such as e.g. at most 8 amino acid substitutions, e.g. at most 6 amino acids substitutions, such as at most 4 amino acids substitutions, e.g. at most 3 amino acids substitutions, such as at most 2 amino acids substitutions. In a further embodiment, there is only 1 amino acid substitution present in the framework regions 1 to 4 of the light chain variable domain taken together or in the in framework regions 1 to 4 of the heavy chain variable domain taken together.

Because the parts of formula I and formula II defined herein as FWs are amino acid sequences that form part of the frame or scaffold of the variable chain regions, substitution within said sequences, in particular in form of conservative amino acid substitutions, will in many cases not affect the binding capability of the anti-cTnT antibody. This is because these amino acids typically are not directly involved in the binding to cTnT, and their substitution for suitable alternative amino acids can be designed such that no alteration in the three-dimensional structure and folding of the protein occurs. On the other hand, such substitutions can provide numerous beneficial effects such as for improved expression in certain hosts or for stabilization of the protein by introduction of e.g. additional disulphide bridges.

The "binding affinity" of an antibody measures the strength of interaction between an epitope on the target antigen and the binding site of the antibody according to the following equation:

$$Kd = kd/ka$$

wherein:
Kd=dissociation equilibrium constant [M]
kd=dissociation rate constant [$s^{-1}$]
ka=association rate constant [$M^{-1} s^{-1}$]

Further relevant parameters for the binding affinity of an antibody are as follows:

$$t/2 = \text{dissociation complex half-life} = \ln 2/kd/60 \text{ [min]}$$

Rmax=response maximum of analyte [RU]
MR: Molar Ratio=ratio of response maximum (Rmax) of analyte In one embodiment a monoclonal antibody to cTnT as disclosed herein above binds to cTnT with a t/2-diss at 37° C. of 10 minutes or longer.

The present invention further relates to an antibody comprising
(i) a light chain variable domain consisting of an amino acid sequence that is at least 85% identical to the light chain variable domain consisting of the amino acid sequence of SEQ ID NO:22, and
(ii) a heavy chain variable domain consisting of an amino acid sequence that has is at least 85% identical to the heavy chain variable domain selected from the amino acid sequences of SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; and SEQ ID NO:32,
wherein the antibody specifically binds to human cardiac troponin T and has a t/2-diss at 37° C. of 10 minutes or longer.

Also disclosed in the present invention is an antibody comprising
(i) a light chain variable domain consisting of an amino acid sequence that is at least 85% identical to the light chain variable domain consisting of the amino acid sequence of SEQ ID NO:22, and
(ii) a heavy chain variable domain of an amino acid sequence selected from the amino acid sequences of SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; and SEQ ID NO:32,
wherein the CDRs comprise the following amino acid sequences (i) in the light chain variable domain a CDR1 comprising the amino acid sequence of SEQ ID NO:2, a CDR2 comprising the amino acid sequence of SEQ ID NO:3, and a CDR3 comprising the amino acid sequence of SEQ ID NO:4, and (ii) in the heavy chain variable domain a CDR1 comprising the amino acid sequence of SEQ ID NO:5; SEQ ID NO:6; or of SEQ ID NO:7, a CDR2 comprising the amino acid sequence of SEQ ID NO:8; or of SEQ ID NO:9, and a CDR3 comprising the amino acid sequence of SEQ ID NO:10; of SEQ ID NO:11; of SEQ ID NO:12; or of SEQ ID NO:13, wherein at least two of the CDRs are selected from a CDR1 of SEQ ID NO:6 or SEQ ID NO:7, a CDR2 of SEQ ID NO:9, and a CDR3 of SEQ ID NO:12, or wherein the CDR1 is of SEQ ID NO:7, the CDR2 is of SEQ ID NO:8, and the CDR3 is of SEQ ID NO:11 or of SEQ ID NO:13, with the proviso that in case a CDR1 of SEQ ID NO:6 is present then either a) the CDR3 is neither SEQ ID NO:11 nor SEQ ID NO:13 or b) the CDR2 and the CDR3 within this antibody are not at the same time of SEQ ID NO:8 and SEQ ID NO:12, respectively,
and wherein the antibody specifically binds to human cardiac troponin T and has a t/2-diss at 37° C. of 10 minutes or longer.

In one embodiment the present disclosure relates to an antibody comprising
(i) a light chain variable domain consisting of the amino acid sequence of SEQ ID NO:22, and
(ii) a heavy chain variable domain consisting of an amino acid sequence selected from the amino acid sequences of SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; and SEQ ID NO:32.

All definitions and specifically exemplified embodiments provided herein above with regard to the anti-cTnT antibody of the invention, in particular the cited degrees and types of variations apply mutatis mutandis.

In accordance with the present invention, novel anti-cTnT antibodies are provided that have improved binding properties to cTnT (better $K_D$ values) and thus enable the detection of cTnT with superior sensitivity as compared to previous assays.

The term "$K_D$" refers to the equilibrium dissociation constant (the reciprocal of the equilibrium binding constant) and is used herein according to the definitions provided in the art. Means and methods for determining the $K_D$ value are as briefly given below and described in detail in the Examples given.

Binding properties of an antibody, e.g., of an anti-cTnT antibody, are best determined via real time biosensor-based molecular interaction measurements, like surface plasmon resonance spectroscopy, for which Biacore technology became a synonym. Experimental details are given in Example 5 and kinetic data is shown in Table 3. For example, the antibody labeled as combination "12" in Table 3 has improved binding properties to cTnT, i.e. an association constant ($k_a$) of 1.18E+06 1/Ms; a dissociation constant ($k_d$) of 3.7 E-04 (translating into a half-time for dissociation of about 31 min and thus an overall affinity constant ($K_D$) of 3.2E-10 M.

The mutated antibodies as disclosed and claimed in the present invention surprisingly on the one hand do not negatively influence the complex formation of the antibody with cTnT, the Ka for all of them is in the same range as for the parent antibody. On the other hand a significant improvement with respect to the stability of the complex formed between cTnT translating into better $K_D$ values could be achieved.

In one embodiment a monoclonal antibody according to the present invention as disclosed herein above binds to cTnT with a t/2-diss at 37° C. of 10 minutes or longer.

Generally, a lower $K_D$ value corresponds to a higher or improved affinity as is well known in the art. In one embodiment, the mutant anti-cTnT antibody has a binding affinity, which is equal or lower than the $K_D$ of the parent antibody having a $K_D$ of 5.8 E-10 M.

The above recited sequences for the variable light and heavy chain regions are the amino acid sequences that have been employed in the appended examples.

The present invention further relates to a nucleic acid molecule encoding a light chain variable region of any one of the antibodies of the invention defined herein above. This nucleic acid molecule is referred to herein as the first nucleic acid molecule of the invention. Furthermore, the present invention also relates to a nucleic acid molecule encoding a heavy chain variable region of any one of the antibodies of the invention defined herein above. This nucleic acid molecule is referred to herein as the second nucleic acid molecule of the invention.

In accordance with the present invention, the term "nucleic acid molecule", also referred to as nucleic acid sequence or polynucleotide herein, includes DNA, such as cDNA or genomic DNA.

The nucleic acid molecules of the invention can e.g. be synthesized by standard chemical synthesis methods and/or recombinant methods, or produced semi-synthetically, e.g. by combining chemical synthesis and recombinant methods. Ligation of the coding sequences to transcriptional regulatory elements and/or to other amino acid encoding sequences can be carried out using established methods, such as restriction digests, ligations and molecular cloning.

In accordance with the present invention, the first nucleic acid molecule of the invention encodes a light chain variable region:
(i) comprising a CDR1 comprising the amino acid sequence of SEQ ID NO:2, a CDR2 comprising the amino acid sequence of SEQ ID NO:3, and a CDR3 comprising the amino acid sequence of SEQ ID NO:4;
(ii) consisting of an amino acid sequence of formula I as defined herein above; or
(iii) consisting of an amino acid sequence that is at least 85% identical to the light chain variable domain consisting of the amino acid sequence of SEQ ID NO:22.

Similarly, the second nucleic acid molecule of the invention encodes a heavy chain variable region
(i) comprising a CDR1 comprising the amino acid sequence of SEQ ID NO:6 or a variant thereof that differs in at most one amino acid substitution, a CDR2 comprising the amino acid sequence of SEQ ID NO:9 or a variant thereof that differs in at most one amino acid substitution, and a CDR3 comprising the amino acid sequence of SEQ ID NO:12 or a variant thereof that differs in at most one amino acid substitution;
(ii) comprising a CDR1 comprising the amino acid sequence of SEQ ID NO:7 or a variant thereof that differs in at most one amino acid substitution, a CDR2 comprising the amino acid sequence of SEQ ID NO:8 or a variant thereof that differs in at most one amino acid substitution, and a CDR3 comprising the amino acid sequence of SEQ ID NO:11 or a variant thereof that differs in at most one amino acid substitution;
(iii) comprising a CDR1 comprising the amino acid sequence of SEQ ID NO:7 or a variant thereof that differs in at most one amino acid substitution, a CDR2 comprising the amino acid sequence of SEQ ID NO:8 or a variant thereof that differs in at most one amino acid substitution, and a CDR3 comprising the amino acid sequence of SEQ ID NO:13 or a variant thereof that differs in at most one amino acid substitution;
(iv) comprising a CDR1 comprising the amino acid sequence of SEQ ID NO:7 or a variant thereof that differs in at most one amino acid substitution, a CDR2 comprising the amino acid sequence of SEQ ID NO:9 or a variant thereof that differs in at most one amino acid substitution, and a CDR3 comprising the amino acid sequence of SEQ ID NO:13 or a variant thereof that differs in at most one amino acid substitution;
(v) comprising a CDR1 comprising the amino acid sequence of SEQ ID NO:6 or a variant thereof that differs in at most one amino acid substitution, a CDR2 comprising the amino acid sequence of SEQ ID NO:9 or a variant thereof that differs in at most one amino acid substitution, and a CDR3 comprising the amino acid sequence of SEQ ID NO:10 or a variant thereof that differs in at most one amino acid substitution;
(vi) comprising a CDR1 comprising the amino acid sequence of SEQ ID NO:7 or a variant thereof that differs in at most one amino acid substitution, a CDR2 comprising the amino acid sequence of SEQ ID NO:9 or a variant thereof that differs in at most one amino acid substitution, and a CDR3 comprising the amino acid sequence of SEQ ID NO:11 or a variant thereof that differs in at most one amino acid substitution;
(vii) comprising a CDR1 comprising the amino acid sequence of SEQ ID NO:7 or a variant thereof that differs in at most one amino acid substitution, a CDR2 comprising the amino acid sequence of SEQ ID NO:9 or a variant thereof that differs in at most one amino acid substitution, and a CDR3 comprising the amino acid sequence of SEQ ID NO:12 or a variant thereof that differs in at most one amino acid substitution;
(viii) comprising a CDR1 comprising the amino acid sequence of SEQ ID NO:7 or a variant thereof that differs in at most one amino acid substitution, a CDR2 comprising the amino acid sequence of SEQ ID NO:9 or a variant thereof that differs in at most one amino acid substitution, and a CDR3 comprising the amino acid sequence of SEQ ID NO:10 or a variant thereof that differs in at most one amino acid substitution;
(ix) comprising a CDR1 comprising the amino acid sequence of SEQ ID NO:7 or a variant thereof that differs in at most one amino acid substitution, a CDR2 comprising the amino acid sequence of SEQ ID NO:8 or a variant thereof that differs in at most one amino acid substitution, and a CDR3 comprising the amino acid sequence of SEQ ID NO:12 or a variant thereof that differs in at most one amino acid substitution;

(x) comprising a CDR1 comprising the amino acid sequence of SEQ ID NO:5 or a variant thereof that differs in at most one amino acid substitution, a CDR2 comprising the amino acid sequence of SEQ ID NO:9 or a variant thereof that differs in at most one amino acid substitution, and a CDR3 comprising the amino acid sequence of SEQ ID NO:12 or a variant thereof that differs in at most one amino acid substitution;

(xi) consisting of an amino acid sequence of formula II as defined herein above;

(xii) consisting of an amino acid sequence that is at least 85% identical to the heavy chain variable domain consisting of the amino acid sequence of SEQ ID NO:23;

(xiii) consisting of an amino acid sequence that is at least 85% identical to the heavy chain variable domain consisting of the amino acid sequence of SEQ ID NO:24; or (xiv) consisting of an amino acid sequence that is at least 85% identical to the heavy chain variable domain consisting of the amino acid sequence of SEQ ID NO:25

(xv) consisting of an amino acid sequence that is at least 85% identical to the heavy chain variable domain consisting of the amino acid sequence of SEQ ID NO:26;

(xvi) consisting of an amino acid sequence that is at least 85% identical to the heavy chain variable domain consisting of the amino acid sequence of SEQ ID NO:27; or (xvii) consisting of an amino acid sequence that is at least 85% identical to the heavy chain variable domain consisting of the amino acid sequence of SEQ ID NO:28

(xviii) consisting of an amino acid sequence that is at least 85% identical to the heavy chain variable domain consisting of the amino acid sequence of SEQ ID NO:29;

(xix) consisting of an amino acid sequence that is at least 85% identical to the heavy chain variable domain consisting of the amino acid sequence of SEQ ID NO:30; or (xx) consisting of an amino acid sequence that is at least 85% identical to the heavy chain variable domain consisting of the amino acid sequence of SEQ ID NO:31

(xxi) consisting of an amino acid sequence that is at least 85% identical to the heavy chain variable domain consisting of the amino acid sequence of SEQ ID NO:32.

The present invention further relates to a vector comprising the first nucleic acid molecule of the invention, i.e. a nucleic acid molecule encoding a light chain variable region of any one of the antibodies of the invention defined herein above. The present invention further relates to a vector comprising the second nucleic acid molecule of the invention, i.e. a nucleic acid molecule encoding a heavy chain variable region of any one of the antibodies of the invention defined herein above. Such vectors are also referred to herein as the "individual vector(s) of the invention".

Many suitable vectors are known to those skilled in molecular biology, the choice of which depends on the desired function. Non-limiting examples of vectors include plasmids, cosmids, viruses, bacteriophages and other vectors used conventionally in e.g. genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994).

In one embodiment, the vector is an expression vector. An expression vector according to this invention is capable of directing the replication and the expression of the nucleic acid molecule of the invention in a host and, accordingly, provides for the expression of the variable chain domains of the anti-troponin T antibodies of the present invention encoded thereby in the selected host. In a further embodiment, the vector(s) comprise(s) further sequences to ensure that not only said variable chain domains of the invention are expressed, but also the full-length IgG antibodies comprising said variable chain domains of the invention.

Expression vectors can for instance be cloning vectors, binary vectors or integrating vectors. Expression comprises transcription of the nucleic acid molecule, for example into a translatable mRNA. In one embodiment, the vector is a eukaryotic expression plasmid for the transient recombinant expression of the heavy chain and/or the light chain of monoclonal rabbit antibodies. Such vectors have been specifically developed for antibody expression but also antibody production by e.g. transient transfection of eukaryotic cells e.g. HEK 293 or derivatives thereof or CHO cells.

Non-limiting examples of vectors include pQE-12, the pUC-series, pBluescript (Stratagene), the pET-series of expression vectors (Novagen) or pCRTOPO (Invitrogen), lambda gal, pJOE, the pBBR1-MCS series, pJB861, pBSMuL, pBC2, pUCPKS, pTACT1, pTRE, pCAL-n-EK, pESP-1, pOP13CAT, the E-027 pCAG Kosak-Cherry (L45a) vector system, pREP (Invitrogen), pCEP4 (Invitrogen), pMClneo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogen), pcDNA3.1, pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Non-limiting examples for plasmid vectors suitable for *Pichia pastoris* comprise e.g. the plasmids pAO815, pPIC9K and pPIC3.5K (all Invitrogen). Another vector suitable for expressing proteins in *Xenopus* embryos, zebrafish embryos as well as a wide variety of mammalian and avian cells is the multipurpose expression vector pCS2+.

Generally, vectors can contain one or more origins of replication (ori) and inheritance systems for cloning or expression, one or more markers for selection in the host, e.g., antibiotic resistance, and one or more expression cassettes. In addition, the coding sequences comprised in the vector can be ligated to transcriptional regulatory elements and/or to other amino acid encoding sequences using established methods. Such regulatory sequences are well known to those skilled in the art and include, without being limiting, regulatory sequences ensuring the initiation of transcription, internal ribosomal entry sites (IRES) (Owens, G. C. et al. [2001] Proc. Natl. Acad. Sci. U.S.A. 98:1471-1476) and optionally regulatory elements ensuring termination of transcription and stabilization of the transcript. Non-limiting examples for such regulatory elements ensuring the initiation of transcription comprise promoters, a translation initiation codon, enhancers, insulators and/or regulatory elements ensuring transcription termination, which are to be included downstream of the nucleic acid molecules of the invention. Further examples include Kozak sequences and intervening sequences flanked by donor and acceptor sites for RNA splicing, nucleotide sequences encoding secretion signals or, depending on the expression system used, signal sequences capable of directing the expressed protein to a cellular compartment or to the culture medium. The vectors may also contain an additional expressible polynucleotide coding for one or more chaperones to facilitate correct protein folding.

Additional examples of suitable origins of replication include, for example, the full length ColE1, a truncated ColEI, the SV40 viral and the M13 origins of replication, while additional examples of suitable promoters include, without being limiting, the cytomegalovirus (CMV) promoter, SV40-promoter, RSV-promoter (Rous sarcoma virus), the lacZ promoter, the tetracycline promoter/operator)(tet$^{p/o}$, chicken β-actin promoter, CAG-promoter (a combination of chicken β-actin promoter and cytomegalovirus immediate-early enhancer), the gai10 promoter, human elongation factor 1α-promoter, AOX1 promoter, GAL1 promoter CaM-kinase promoter, the lac, trp or tac promoter, the T7 or T5 promoter, the lacUV5 promoter, the *Autographa californica* multiple nuclear polyhedrosis virus (AcMNPV) polyhedral promoter or a globin intron in mammalian and other animal cells. One example of an enhancer is e.g. the SV40-enhancer. Non-limiting additional examples for regulatory elements ensuring transcription termination include the SV40-poly-A site, the tk-poly-A site, the rho-independent lpp terminator or the AcMNPV polyhedral polyadenylation signals. Further non-limiting examples of selectable markers include dhfr, which confers resistance to methotrexate (Reiss, Plant Physiol. (Life Sci. Adv.) 13 (1994), 143-149), npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to blasticidin S (Tamura, Biosci. Biotechnol. Biochem. 59 (1995), 2336-2338).

In a further embodiment, the vector is a eukaryotic expression plasmid containing an expression cassette consisting of a 5' CMV promoter including Intron A, and a 3' BGH polyadenylation sequence. In addition to the expression cassette, the plasmid can contain a pUC18-derived origin of replication and a beta-lactamase gene conferring ampicillin resistance for plasmid amplification in *E. coli*. For secretion of the antibodies, a eukaryotic leader sequence can be cloned 5' of the antibody gene.

Suitable bacterial expression hosts comprise e.g. strains derived from JM83, W3110, KS272, TG1, K12, BL21 (such as BL21(DE3), BL21(DE3)PlysS, BL21(DE3)RIL, BL21 (DE3)PRARE) or Rosetta. For vector modification, PCR amplification and ligation techniques, see Sambrook & Russel [2001] (Cold Spring Harbor Laboratory, NY).

The nucleic acid molecules and/or vectors of the invention can be designed for introduction into cells by e.g. chemical based methods (polyethylenimine, calcium phosphate, liposomes, DEAE-dextrane, nucleofection), non chemical methods (electroporation, sonoporation, optical transfection, gene electrotransfer, hydrodynamic delivery or naturally occurring transformation upon contacting cells with the nucleic acid molecule of the invention), particle-based methods (gene gun, magnetofection, impalefection) phage vector-based methods and viral methods. For example, expression vectors derived from viruses such as retroviruses, vaccinia virus, adeno-associated virus, herpes viruses, Semliki Forest Virus or bovine papilloma virus, may be used for delivery of the nucleic acid molecules into targeted cell population. Additionally, baculoviral systems can also be used as vector in eukaryotic expression system for the nucleic acid molecules of the invention. In one embodiment, the nucleic acid molecules and/or vectors of the invention are designed for transformation of chemical competent *E. coli* by calcium phosphate and/or for transient transfection of HEK293 and CHO by polyethylenimine- or lipofectamine-transfection.

The present invention further relates to a vector comprising:
(i) a nucleic acid molecule encoding a light chain variable domain according to option (i) defined herein above and a heavy chain variable domain according to option (i) defined herein above;
(ii) a nucleic acid molecule encoding a light chain variable domain according to option (ii) defined herein above and a heavy chain variable domain according to option (ii) defined herein above; or
(iii) a nucleic acid molecule encoding a light chain variable domain according to option (iii) defined herein above and a heavy chain variable domain according to option (iii) defined herein above.

In one embodiment, the vector is an expression vector.

All definitions and specifically exemplified embodiments provided herein above with regard to the vector of the invention, in particular vector types or the regulatory sequences apply mutatis mutandis. This second type of vector relates to a vector comprising at least two nucleic acid molecules, namely one encoding a light chain variable domain and one encoding a heavy chain variable domain. As is evident from the above combinations, the light chain variable domain and heavy chain variable domain are combined in the vector such that the expression of a functional anti-cTnT antibody of the invention is enabled. This second type of vector is also referred to herein as the "combination vector of the invention".

The present invention further relates to a host cell or non-human host comprising:
(i) the combination vector of the invention; or
(ii) the individual vector of the invention comprising the first nucleic acid molecule of the invention, i.e. a nucleic acid molecule encoding a light chain variable region in accordance with the invention and the individual vector of the invention comprising the second nucleic acid molecule of the invention, i.e. a nucleic acid molecule encoding a heavy chain variable region of the invention, wherein these two vectors comprise the nucleic acid molecules encoding for matching light chain and heavy chain variable regions as defined in options (i) to (iii) above.

The host cell can be any prokaryotic or eukaryotic cell. The term "prokaryote" is meant to include all bacteria which can be transformed, transduced or transfected with DNA or RNA molecules for the expression of a protein of the invention. Prokaryotic hosts may include gram negative as well as gram positive bacteria such as, for example, *E. coli, S. typhimurium, Serratia marcescens, Corynebacte-*

*rium (glutamicum), Pseudomonas (fluorescens), Lactobacillus, Streptomyces, Salmonella* and *Bacillus subtilis.*

The term "eukaryotic" is meant to include yeast, higher plant, insect and mammalian cells. Typical mammalian host cells include, Hela, HEK293, H9, Per.C6 and Jurkat cells, mouse NIH3T3, NS/0, SP2/0 and C127 cells, COS cells, e.g. COS 1 or COS 7, CV1, quail QC1-3 cells, mouse L cells, mouse sarcoma cells, Bowes melanoma cells and Chinese hamster ovary (CHO) cells. Exemplary mammalian host cells in accordance with the present invention are CHO cells. Other suitable eukaryotic host cells include, without being limiting, chicken cells, such as e.g. DT40 cells, or yeasts such as *Saccharomyces cerevisiae, Pichia pastoris, Schizosaccharomyces pombe* and *Kluyveromyces lactis.* Insect cells suitable for expression are e.g. *Drosophila* S2, *Drosophila* Kc, *Spodoptera* Sf9 and Sf21 or *Trichoplusia* Hi5 cells. Suitable zebrafish cell lines include, without being limiting, ZFL, SJD or ZF4.

The described vector(s) can either integrate into the genome of the host or can be maintained extrachromosomally. Once the vector has been incorporated into the appropriate host, the host is maintained under conditions suitable for high level expression of the nucleic acid molecules, and as desired, the collection and purification of the antibody of the invention may follow. Appropriate culture media and conditions for the above described host cells are known in the art.

In one embodiment, the recited host is a mammalian cell, such as a human cell or human cell line. In a further embodiment, the host cell transformed with the vector(s) of the invention is HEK293 or CHO. In yet a further embodiment, the host cell transformed with the vector(s) of the invention is CHO. These host cells as well as suitable media and cell culture conditions have been described in the art, see e.g. Baldi L. et al., Biotechnol Prog. 2005 January-February; 21(1):148-53, Girard P. et al., Cytotechnology. 2002 January; 38(1-3):15-21 and Stettler M. et al., Biotechnol Prog. 2007 November-December; 23(6):1340-6.

With regard to the term "vector comprising" in accordance with the present invention it is understood that further nucleic acid sequences are present in the vectors that are necessary and/or sufficient for the host cell to produce an anti-cTnT antibody of the invention. Such further nucleic acid sequences are e.g. nucleic acid sequences encoding the remainder of the light chain as well as nucleic acid sequences encoding the remainder of the heavy chain.

The host cell or non-human host, in accordance with the present invention, comprises either one vector encoding both the light chain and heavy chain variable regions as defined herein above or it comprises two separate vectors, wherein one vector carries a nucleic acid molecule encoding a light chain variable region in accordance with the present invention and the second vector carries a nucleic acid molecule encoding a matching heavy chain variable region in accordance with the present invention. Thus, where the first vector carries a nucleic acid molecule encoding a light chain variable region in accordance with option (i) herein above, then the second vector carries a nucleic acid molecule encoding a heavy chain variable region also in accordance with option (i) above. The same applies mutatis mutandis to options (ii) and (iii).

Accordingly, in each case, expression of those nucleic acid molecules is linked to each other that are required to be present within one antibody molecule to ensure the production of an anti-cTnT antibody of the invention consisting of the binding capabilities described herein above.

The host cells in accordance with this embodiment may e.g. be employed to produce large amounts of the anti-cTnT antibodies of the present invention. Said host cells are produced by introducing the above described vector(s) into the host. The presence of said vector(s) in the host then mediates the expression of the nucleic acid molecules encoding the above described light chain variable domains and heavy chain variable domains of the anti-cTnT antibodies of the invention. As described herein above, the vector(s) of the invention can comprise further sequences enabling the expression of full length IgG antibodies, thereby resulting in the production of full length IgG antibodies by the host cells, wherein said antibodies are characterized by the presence of the variable light and/or heavy chain domains in accordance with the present invention.

The present invention further relates to a method for the production of an antibody that specifically binds to cTnT of SEQ ID NO:1, the method comprising culturing the host cell of the invention under suitable conditions and isolating the antibody produced.

In accordance with this embodiment, the vector(s) present in the host of the invention is/are either (an) expression vector(s), or the vector(s) mediate(s) the stable integration of the nucleic acid molecule(s) of present invention into the genome of the host cell in such a manner that expression thereof is ensured. Means and methods for selection a host cell in which the nucleic acid molecules encoding the respective light and heavy chain domains of the anti-cTnT antibody of the present invention have been successfully introduced such that expression of the antibody is ensured are well known in the art and have been described (Browne, S. M. & Al-Rubeai, M. [2007] Trends Biotechnol. 25:425-432; Matasci, M et al. [2008] Drug Discov. Today: Technol. 5:e37-e42; Wurm, F. M. [2004] Nat. Biotechnol. 22:1393-1398).

Suitable conditions for culturing prokaryotic or eukaryotic host cells are well known to the person skilled in the art. For example, bacteria such as e.g. *E. coli* can be cultured under aeration in Luria Bertani (LB) medium, typically at a temperature from 4 to about 37° C. To increase the yield and the solubility of the expression product, the medium can be buffered or supplemented with suitable additives known to enhance or facilitate both. In those cases where inducible promoters control the nucleic acid molecules of the invention in the vector(s) present in the host cell, expression of the polypeptide can be induced by addition of an appropriate inducing agent, such as e.g. anhydrotetracycline. Suitable expression protocols and strategies have been described in the art (e.g. in Dyson, M. R., et al. (2004). BMC Biotechnol. 4, 32-49 and in Baldi, L. et al. (2007). Biotechnol. Lett. 29, 677-684) and can be adapted to the needs of the specific host cells and the requirements of the protein to be expressed, if required.

Depending on the cell type and its specific requirements, mammalian cell culture can e.g. be carried out in RPMI, Williams' E or DMEM medium containing 10% (v/v) FCS, 2 mM L-glutamine and 100 U/ml penicillin/streptomycin. The cells can be kept e.g. at 37° C. or at 41° C. for DT40 chicken cells, in a 5% $CO_2$, water-saturated atmosphere.

A suitable medium for insect cell culture is e.g. TNM+ 10% FCS, SF900 or HyClone SFX-Insect medium. Insect cells are usually grown at 27° C. as adhesion or suspension cultures.

Suitable expression protocols for eukaryotic or vertebrate cells are well known to the skilled person and can be retrieved e.g. from Sambrook, J & Russel, D. W. [2001] (Cold Spring Harbor Laboratory, NY).

In one embodiment, the method is carried out using mammalian cells, such as e.g. CHO or HEK293 cells. In a further embodiment, the method is carried out using CHO cells.

Depending upon the host employed in a recombinant production procedure, the antibody expressed may be glycosylated or may be non-glycosylated. In one embodiment, a plasmid or a virus is used containing the coding sequence of the antibody of the invention and genetically fused thereto an N-terminal FLAG-tag and/or C-terminal His-tag. In a further embodiment, the length of said FLAG-tag is about 4 to 8 amino acids, such as e.g. exactly 8 amino acids. An above described vector can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, loc cit.).

The transformed hosts can be grown in bioreactors and cultured according to techniques known in the art to achieve optimal cell growth. The antibody of the invention can then be isolated from the growth medium. The isolation and purification of the, e.g., microbially expressed antibodies of the invention may be by any conventional means such as, e.g., affinity chromatography (for example using a fusion-tag such as the Strep-tag II or the $His_6$ tag), gel filtration (size exclusion chromatography), anion exchange chromatography, cation exchange chromatography, hydrophobic interaction chromatography, high pressure liquid chromatography (HPLC), reversed phase HPLC or immunoprecipitation. These methods are well known in the art and have been generally described, e.g. in Sambrook, J & Russel, D. W. [2001] (Cold Spring Harbor Laboratory, NY).

It will be appreciated that in accordance with the present invention, the term "isolating the antibody produced" refers to the isolation of the anti-cTnT antibody of the present invention.

The present invention further relates to a composition comprising at least one of:
 (i) the antibody of the invention,
 (ii) the nucleic acid molecule of the invention,
 (iii) the vector of the invention,
 (iv) the host cell of the invention, and/or
 (v) the antibody produced by the method of the invention.

The term "composition", as used in accordance with the present invention, relates to a composition which comprises at least one of the recited compounds. It may, optionally, comprise further molecules capable of altering the characteristics of the compounds of the invention thereby, for example, stabilizing, modulating and/or enhancing their function. The composition may be in solid or liquid form and may be, inter alia, in the form of (a) powder(s), (a) tablet(s) or (a) solution(s).

The components of the composition can be packaged in a container or a plurality of containers, for example, sealed ampoules or vials, as an aqueous solution or as a lyophilized formulation for reconstitution. As an example of a lyophilized formulation, 10-ml vials are filled with 5 ml of 1% (w/v) or 10% (w/v) aqueous solution, and the resulting mixture is lyophilized. A solution for use is prepared by reconstituting the lyophilized compound(s) using either e.g. water-for-injection for therapeutic uses or another desired solvent, e.g. a buffer, for diagnostic purposes. Preservatives and other additives may also be present such as, for example, antimicrobials, anti-oxidants, chelating agents, and inert gases and the like.

The various components of the composition may be packaged as a kit with instructions for use.

In one embodiment, the composition of the invention is a composition enabling the skilled person to carry out in vitro or ex vivo methods well known in the art, for example, methods such as immunoassays.

Examples of immunoassays which can utilize the antibodies of the invention are immunoassays in either a direct or indirect format. Examples of such immunoassays are the enzyme linked immunosorbent assay (ELISA), enzyme immunoassay (EIA), radioimmunoassay (RIA), or immuno assays based on detection of luminescence, fluorescence, chemiluminescence or electrochemiluminescence.

Cardiac troponin T (cTnT) is best detected by a sandwich immuno assay as for example disclosed in U.S. Pat. Nos. 6,333,397 and 6,376,206, respectively, and confirmed in essentially all subsequent generations of assays for measurement of cTnT. In the fifth generation cTnT-assay, the high sensitivity assay for cTnT (hs-cTnT) sold by Roche Diagnostics, Germany, still the sandwich immuno assay principle is employed. This assay is a high sensitivity assay, because it can detect cTnT with a lower limit of detection (LOD) of 5 ng/ml. This good LOD is reached despite the overall very short incubation time of 9 or 18 min, respectively, dependent on the assay protocol used. In this assay a sandwich is formed comprising a biotinylated capture antibody and a ruthenylated detection antibody. This complex is bound to streptavidin coated magnetic beads and unbound materials are washed out. As obvious to the skilled artisan it is quite critical, if the Kd is not outstanding, because some dissociation will occur and lead to reduced signals, directly translation into reduced LOD.

As obvious to the skilled artisan it will be advantageous to use an antibody according to the present invention in a method for detection of cTnT.

In one embodiment the present disclosure relates to a method of detecting cTnT in a sample, the method comprising the steps of: a) contacting the sample with an anti-cTnT antibody according to the present disclosure for a time and under conditions sufficient for the formation of an anti-cTnT antibody/cTnT complex; and b) measuring the anti-cTnT antibody/cTnT complex, wherein the amount of that complex is indicative for the concentration of cTnT in the sample. The terminology "/" e.g. in "anti-cTnT antibody/cTnT complex" is used in order to indicate that a non-covalent complex is formed between the anti-cTnT antibody on the one hand and the cTnT on the other hand.

In one embodiment the present invention relates to a method of detecting cTnT in a sample comprising the steps of: a) contacting the sample with a first antibody to cTnT and a second antibody to cTnT, wherein the second antibody is detectably labeled, for a time and under conditions sufficient to form a first anti-cTnT antibody/cTnT/second anti-cTnT antibody complex; and b) measuring the complex formed in (a), wherein the amount of that complex is indicative for the concentration of cTnT in the sample and wherein either the first or the second antibody is an antibody according to the present invention.

As obvious to the skilled artisan the sample can be contacted with the first and the second antibody in any desired order, i.e. first antibody first, the second antibody; second antibody first than first antibody, or simultaneously, for a time and under conditions sufficient to form a first anti-cTnT antibody/cTnT/second anti-cTnT antibody complex.

As the skilled artisan will readily appreciate it is nothing but routine experimentation to establish the time and conditions that are appropriate or that are sufficient for the formation of a complex either between the specific anti cTnT antibody and the cTnT antigen/analyte (=anti-cTnT antibody/cTnT complex) or the formation of the secondary or sandwich complex comprising the first antibody to cTnT, the cTnT (the analyte) and the second anti-cTnT antibody complex (=first anti-cTnT antibody/cTnT/second anti-cTnT antibody complex).

The detection of the anti-cTnT antibody/cTnT complex can be performed by any appropriate means. The person skilled in the art is absolutely familiar with such means/methods.

The term "sample" or "sample of interest" or "test sample" are used interchangeably herein. The sample is an in vitro sample, it will be analysed in vitro and not transferred back into the body. Examples of samples include but are not limited to fluid samples such as blood, serum, plasma, synovial fluid, urine, saliva, and lymphatic fluid, or solid samples such as tissue extracts, cartilage, bone, synovium, and connective tissue. In one embodiment the sample is selected from blood, serum, plasma, synovial fluid and urine. In one embodiment the sample is selected from blood, serum and plasma. In one embodiment the sample is serum or plasma.

The term "reference sample" as used herein, refers to a sample which is analyzed in a substantially identical manner as the sample of interest and whose information is compared to that of the sample of interest. A reference sample thereby provides a standard allowing for the evaluation of the information obtained from the sample of interest. A reference sample may be derived from a healthy or normal tissue, organ or individual, thereby providing a standard of a healthy status of a tissue, organ or individual. Differences between the status of the normal reference sample and the status of the sample of interest may be indicative of the risk of disease development or the presence or further progression of such disease or disorder. A reference sample may be derived from an abnormal or diseased tissue, organ or individual thereby providing a standard of a diseased status of a tissue, organ or individual. Differences between the status of the abnormal reference sample and the status of the sample of interest may be indicative of a lowered risk of disease development or the absence or bettering of such disease or disorder The terms "elevated" or "increased" level of an indicator refer to the level of such indicator in the sample being higher in comparison to the level of such indicator in a reference or reference sample. E.g. a protein that is detectable in higher amounts in a fluid sample of one individual suffering from a given disease than in the same fluid sample of individuals not suffering from said disease, has an elevated level.

In certain embodiments a sandwich will be formed comprising a first antibody to cTnT, the cTnT (analyte) and the second antibody to cTnT, wherein the second antibody is detectably labeled.

Numerous labels (also referred to as dyes) are available which can be generally grouped into the following categories, all of them together and each of them representing embodiments according the present disclosure:

(a) Fluorescent Dyes

Fluorescent dyes are e.g. described by Briggs et al "Synthesis of Functionalized Fluorescent Dyes and Their Coupling to Amines and Amino Acids," J. Chem. Soc., Perkin-Trans. 1 (1997) 1051-1058).

Fluorescent labels or fluorophores include rare earth chelates (europium chelates), fluorescein type labels including FITC, 5-carboxyfluorescein, 6-carboxy fluorescein; rhodamine type labels including TAMRA; dansyl; Lissamine; cyanines; phycoerythrins; Texas Red; and analogs thereof. The fluorescent labels can be conjugated to an aldehyde group comprised in target molecule using the techniques disclosed herein. Fluorescent dyes and fluorescent label reagents include those which are commercially available from Invitrogen/Molecular Probes (Eugene, Oregon, USA) and Pierce Biotechnology, Inc. (Rockford, Ill.).

(b) Luminescent Dyes

Luminescent dyes or labels can be further subcategorized into chemiluminescent and electrochemiluminescent dyes.

The different classes of chemiluminogenic labels include luminol, acridinium compounds, coelenterazine and analogues, dioxetanes, systems based on peroxyoxalic acid and their derivatives. For immunodiagnostic procedures predominantly acridinium based labels are used (a detailed overview is given in Dodeigne C. et al., Talanta 51 (2000) 415-439).

The labels of major relevance used as electrochemiluminescent labels are the Ruthenium- and the Iridium-based electrochemiluminescent complexes, respectively. Electrochemiluminescense (ECL) proved to be very useful in analytical applications as a highly sensitive and selective method. It combines analytical advantages of chemiluminescent analysis (absence of background optical signal) with ease of reaction control by applying electrode potential. In general Ruthenium complexes, especially [Ru (Bpy)3]2+ (which releases a photon at ~620 nm) regenerating with TPA (Tripropylamine) in liquid phase or liquid-solid interface are used as ECL-labels. Recently also Iridium-based ECL-labels have been described (WO2012107419(A1)).

(c) Radioactive labels make use of radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi.

(d) Metal-chelate complexes suitable as labels for imaging and therapeutic purposes are well-known in the art (US 2010/0111856; U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61(2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

In one embodiment a sandwich will be formed comprising a first antibody to cTnT, the cTnT (analyte) and the second antibody to cTnT, wherein the second antibody is detectably labeled and wherein the first anti-cTnT antibody is capable of binding to a solid phase or is bound to a solid phase.

In one embodiment the anti-cTnT antibody disclosed in the present invention is used in an immuno assay to measure cTnT. In one embodiment the anti-cTnT antibody disclosed herein above is used in a sandwich-type immuno assay. In one embodiment the anti-cTnT antibody disclosed in the present invention is used as a detection antibody. In one embodiment the anti-cTnT antibody as disclose herein is detectably labeled with a luminescent dye, especially a chemiluminescent dye or an electrochemiluminescent dye.

These and other embodiments are disclosed and encompassed by the description and Examples of the present invention. Further literature concerning any one of the methods, uses and compounds to be employed in accordance with the present invention may be retrieved from public libraries and databases, using for example electronic devices. For example, the public database "Medline", available on the Internet, may be utilized, for example in the World Wide Web under ncbi.nlm nih.gov/PubMed/medline.html. Further databases and addresses available in the World Wide Web, such as ncbi.nlm nih.gov/, fmi.ch/biology/research_tools.html,tigr.org/, or infobiogen.fr/, are known to the person skilled in the art and can also be obtained using the address in the World Wide Web under lycos.com.

Unless otherwise defined, all technical and scientific terms used herein have the same meaning as commonly understood by one of ordinary skill in the art to which this invention belongs. In case of conflict, the patent specification, including definitions, will prevail.

All amino acid sequences provided herein are presented starting with the most N-terminal residue and ending with the most C-terminal residue (N→C), as customarily done in the art, and the one-letter or three-letter code abbreviations as used to identify amino acids throughout the present invention correspond to those commonly used for amino acids.

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims.

Certain aspects of the invention are also illustrated by way of the attached figures.

DESCRIPTION OF THE FIGURES

FIGS. 1A-1C: Construction of a DNA library encoding amino acid substitutions within one or more of the heavy chain CDRs FIG. 1A: Production of the heavy chain fragments required in the construction of the mutant library (step1). In the first round (PCR 1) three different heavy chain fragments corresponding to fragments 1, 3 and 4, respectively were generated by aid of corresponding primer sets. The light grey stretches indicate the CDRs. The backbone sequence is given in black. Horizontal arrows indicate the primers used. Vertical arrows point to the results of the PCR. The short 42 bp oligonucleotide (fragment 2) which is crossed out in the Figure was not obtained by PCR but was separately chemically synthesized.

FIG. 1B: HC library synthesis by CDR single amino acid randomization. In the second step PCR 2, the four fragments obtained as described in FIG. 1A served as templates (black lines). Horizontal arrows with a cross indicate the polynucleotide libraries each comprising a degenerated NNK codon for each CDR codon position. These polynucleotide libraries in addition comprise sequence stretches capable of hybridizing to one or two of the fragments of step 1 as required and indicated. Forward and reverse primers, respectively, (small arrows) were used to perform the respective PCRs.

FIG. 1C: Final step of library synthesis: The additional sequence stretches capable of hybridizing to one or two of the fragments of step 1 are needed to perform the final step in production of the HC library, i.e. an overlapping PCR using all four products of PCR 2. Terminal primers (F1A; R1A) are used and the fragments themselves act as mega primers in this overlapping PCR.

The following Examples illustrate the invention:

EXAMPLE 1: MATERIALS & GENERAL METHODS

Recombinant DNA Techniques

Standard methods were used to manipulate DNA as described in Sambrook, J. et al., Molecular Cloning: A laboratory manual; Cold Spring Harbor Laboratory Press, Cold Spring Harbor, N.Y., 1989. The molecular biological reagents were used according to the manufacturer's instructions.

DNA Sequence Determination

DNA sequences were determined by double strand sequencing performed at Microsynth AG (Balgach, Switzerland).

DNA and Protein Sequence Analysis and Sequence Data Management

Vector NT1 Advance suite version 11.5.0 was used for sequence creation, mapping, analysis, annotation and illustration.

Protein Chemistry and Labeling Techniques

Standard protein chemistry and labeling techniques are provided e.g. in Hermanson, G. "Bioconjugate Techniques" 3rd Edition (2013) Academic Press.

Bioinformatics

Bioinformatics methods are provided in e.g. Keith J. M. (ed.) "Bioinformatics" Vol. I and Vol. II, Methods in Molecular Biology Vol. 1525 and Vol. 1526 (2017) Springer, and in Martin, A. C. R. & Allen, J. "Bioinformatics Tools for Analysis of Antibodies" in: Dübel S. & Reichert J. M. (eds.) "Handbook of Therapeutic Antibodies" Wiley-VCH (2014).

Electrochemiluminescent Immunoassays

Immunoassays and related methods are provided in e.g. Wild D. (ed.) "The Immunoassay Handbook" 4th Edition (2013) Elsevier. Ruthenium complexes as electrochemiluminescent labels are provided in e.g. Staffilani M. et al. Inorg. Chem. 42 (2003) 7789-7798. Typically, for the performance of electrochemiluminescence (ECL) based immunoassays an Elecsys 2010 analyzer or a successor system was used, e.g. a Roche analyzer (Roche Diagnostics GmbH, Mannheim Germany) such as E170, cobas e 601 module, cobas e 602 module, cobas e 801 module, and cobas e 411, and Roche Elecsys assays designed for these analyzers, each used under standard conditions, if not indicated otherwise.

EXAMPLE 2: LIBRARY CONSTRUCTION

Figure 1A:
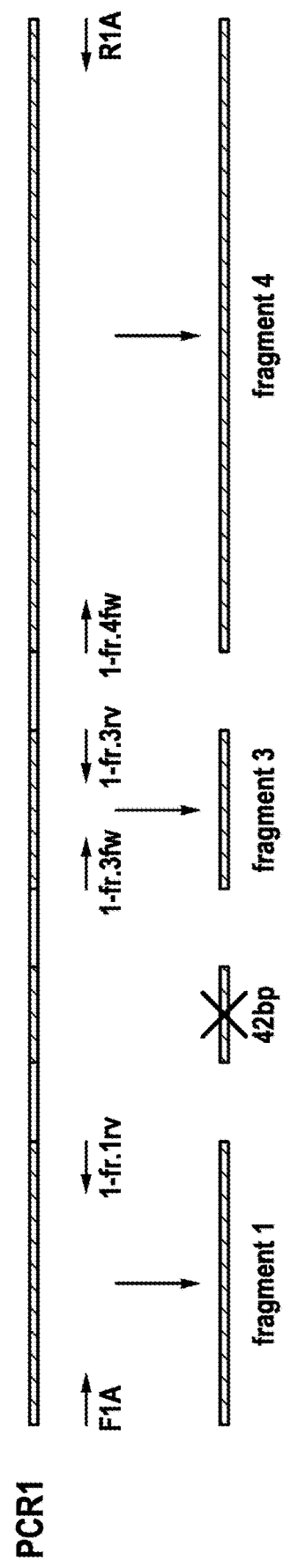

The parent antibody variable heavy chain is of murine origin (SEQ ID NO:34). A library comprising mutated HCCDRs was constructed with the goal of a single amino acid randomization in HCCDR1, HCCDR2 and/or HCCDR3, respectively. In a first step four DNA fragments were generated each encoding one of the four different parental antibody framework regions. Framework regions 1, 3 and 4 were obtained by polymerase chain reaction in house, the short fragment 2 (42 bp), representing framework region 2, was ordered at Metabion international AG (cf. FIG. 1A). The fragments were gel purified and quantified. 100 ng of one of these DNA fragments was used as a polynucleotide template in each of the four add-on PCR reaction mixtures. The CDR regions were added by use of a polynucleotide library comprising the same number of codons as the parent CDR, wherein the members of said library were designed to comprise library members with one NNK codon for each of the respective codon position in the respective HCCDR. The polynucleotides in the CDR library in addition comprised sequences capable of hybridizing to the framework region neighboring to the respective CDR. Terminal primers were used for nested PCR amplification. Thereby (cf. FIG. 1B) four DNA fragments with partially overlapping sequences were generated. Overlapping PCR, with terminal primers hybridizing to the 3' end of the FW1 sequence and to the 5' end of the FW4 sequence, was performed to connect the four fragments to a linear DNA library construct (cf. FIG. 1C). A typical PCR reaction was filled with PCR grade water to a 100 µl reaction mix containing 10 µl 10×PCR buffer with MgSO4, 200 µM dNTP mix, 0.5 µM forward primer and reverse primer, 250 ng DNA template, 5 units Pwo DNA polymerase. A typical PCR started with initial template denaturation at 94° C. for 5 min, employed 30 cycles (94° C. 2 min, 60° C. 45 sec, 72° C. 1 min) and contained a final elongation step at 72° C. for 5 min Primers, templates and fragment sequences are listed in Table 1. The library fragments contained all necessary regulatory sequences for a successful transcription and translation in a cell-free system. The skilled artisan is able to generate such library by following state of the art methods, see e.g. Hanes, J. & Pluckthun, A. (1997), "In vitro selection and evolution of functional proteins by using ribosome display", Proc Natl Acad Sci U.S.A. 94, 4937-42. 250 ng of the DNA library thus generated, covering the three HC CDRs and corresponding to about $5 \cdot 10^{11}$ library members were used for the in vitro display approach.

TABLE 1

Sequences used in the generation of the anti-cTnT Fab fragment library

|  |  | SEQ ID NO: |
|---|---|---|
| PCR 1 |  |  |
| F1A | CGAAATTAATACGACTCACTATAGGGAGACCACAACGGTTTCCC | 35 |
| 1-fr.1rv | GGTAAAGGTATAGCCGCTCG | 36 |
| 1-fr.3fw | CCAGAAATTTAAGGATAAAGCGACCC | 37 |
| 1-fr.3rv | GGTCGCGCAATAATACACCG | 38 |
| 1-fr.4fw | CGGTGTATTATTGCGCGACC | 39 |
| R1A | AACCCCCGCATAGGCTGGGGGTTGGAAAGCCTCTGAGGACCAGCACG | 40 |

TABLE 1-continued

Sequences used in the generation of the anti-cTnT Fab fragment library

PCR 2

| | | |
|---|---|---|
| Fragment 1 Frt | GGGAGACCACAACGGTTTCCCTCTAGAAATAATTTTGTTTAACTTTAAGAAGGAGATATACAT | 41 |
| 2-H1 rv mix | | |
| 2-H1 rv1 | GCTCTGTTTCACCCATTTCATATAATAMNNGGTAAAGGTATAGC | 42 |
| 2-H1 rv2 | GCTCTGTTTCACCCATTTCATATAMNNATCGGTAAAGGTATAGC | 43 |
| 2-H1 rv3 | GCTCTGTTTCACCCATTTCAMNNAATAATCGGTAAAGGTATAGC | 44 |
| 2-H1 rv4 | GCTCTGTTTCACCCATTTMNNATAATAATCGGTAAAGGTATAGC | 45 |
| 2-H1 rv5 | GCTCTGTTTCACCCAMNNCATATAATAATCGGTAAAGGTATAGC | 46 |
| 2-fr.1 rv | CCATGGCTCTGTTTCACCC | 47 |
| Fragment 2 2-fr.2 fw | CGAGCGGCTATACCTTTACC | 48 |
| 2-H1 fw mix | | |
| 2-H1 fw1 | GCTATACCTTTACCNNKTATTATATGAAATGGGTGAAACAGAGC | 49 |
| 2-H1 fw2 | GCTATACCTTTACCGATNNKTATATGAAATGGGTGAAACAGAGC | 50 |
| 2-H1 fw3 | GCTATACCTTTACCGATTATNNKATGAAATGGGTGAAACAGAGC | 51 |
| 2-H1 fw4 | GCTATACCTTTACCGATTATTATNNKAAATGGGTGAAACAGAGC | 52 |
| 2-H1 fw5 | GCTATACCTTTACCGATTATTATATGNNKTGGGTGAAACAGAGC | 53 |
| 2-H2 rv mix | | |
| 2-H2 rv1 | CCTTAAATTTCTGGTTATAAAAGGTTTCGCCGTTGTTCGGATTAATMNNGCCAATCCATTCCAGG | 54 |
| 2-H2 rv2 | CCTTAAATTTCTGGTTATAAAAGGTTTCGCCGTTGTTCGGATTMNNATCGCCAATCCATTCCAGG | 55 |
| 2-H2 rv3 | CCTTAAATTTCTGGTTATAAAAGGTTTCGCCGTTGTTCGGMNNAATATCGCCAATCCATTCCAGG | 56 |
| 2-H2 rv4 | CCTTAAATTTCTGGTTATAAAAGGTTTCGCCGTTGTTMNNATTAATATCGCCAATCCATTCCAGG | 57 |
| 2-H2 rv5 | CCTTAAATTTCTGGTTATAAAAGGTTTCGCCGTTMNNCGGATTAATATCGCCAATCCATTCCAGG | 58 |
| 2-H2 rv6 | CCTTAAATTTCTGGTTATAAAAGGTTTCGCCMNNGTTCGGATTAATATCGCCAATCCATTCCAGG | 59 |
| 2-H2 rv7 | CCTTAAATTTCTGGTTATAAAAGGTTTCMNNGTTGTTCGGATTAATATCGCCAATCCATTCCAGG | 60 |
| 2-H2 rv8 | CCTTAAATTTCTGGTTATAAAAGGTMNNGCCGTTGTTCGGATTAATATCGCCAATCCATTCCAGG | 61 |
| 2-H2 rv9 | CCTTAAATTTCTGGTTATAAAAMNNTTCGCCGTTGTTCGGATTAATATCGCCAATCCATTCCAGG | 62 |
| 2-H2 rv10 | CCTTAAATTTCTGGTTATAMNNGGTTTCGCCGTTGTTCGGATTAATATCGCCAATCCATTCCAGG | 63 |
| 2-fr.2 rv | GGGTCGCTTTATCCTTAAATTTCTGG | 64 |
| Fragment 3 2-fr.3 fw | GCAAAAGCCTGGAATGGATTGGC | 65 |
| 2-H2 fw mix | | |
| 2-H2 fw1 | CCTGGAATGGATTGGCNNKATTAATCCGAACAACGGCGAAACCTTTATAACCAGAAATTTAAGG | 66 |
| 2-H2 fw2 | CCTGGAATGGATTGGCGATNNKAATCCGAACAACGGCGAAACCTTTATAACCAGAAATTTAAGG | 67 |

TABLE 1-continued

Sequences used in the generation of the anti-cTnT Fab fragment library

| | | |
|---|---|---|
| 2-H2 fw3 | CCTGGAATGGATTGGCGATATTNNKCCGAACAACGGCGAAACCT TTTATAACCAGAAATTTAAGG | 68 |
| 2-H2 fw4 | CCTGGAATGGATTGGCGATATTAATNNKAACAACGGCGAAACCT TTTATAACCAGAAATTTAAGG | 69 |
| 2-H2 fw5 | CCTGGAATGGATTGGCGATATTAATCCGNNKAACGGCGAAACCT TTTATAACCAGAAATTTAAGG | 70 |
| 2-H2 fw6 | CCTGGAATGGATTGGCGATATTAATCCGAACNNKGGCGAAACCT TTTATAACCAGAAATTTAAGG | 71 |
| 2-H2 fw7 | CCTGGAATGGATTGGCGATATTAATCCGAACAACNNKGAAACCT TTTATAACCAGAAATTTAAGG | 72 |
| 2-H2 fw8 | CCTGGAATGGATTGGCGATATTAATCCGAACAACGGCNNKACCT TTTATAACCAGAAATTTAAGG | 73 |
| 2-H2 fw9 | CCTGGAATGGATTGGCGATATTAATCCGAACAACGGCGAANNKT TTTATAACCAGAAATTTAAGG | 74 |
| 2-H2 fw10 | CCTGGAATGGATTGGCGATATTAATCCGAACAACGGCGAAACCN NKTATAACCAGAAATTTAAGG | 75 |
| 2-H3 rv mix | | |
| 2-H3 rv1 | GGTACCCTGGCCCCAATAATCAAACACMNNGGTCGCGCAATAAT ACACC | 76 |
| 2-H3 rv2 | GGTACCCTGGCCCCAATAATCAAAMNNGCGGGTCGCGCAATAAT ACACC | 77 |
| 2-H3 rv3 | GGTACCCTGGCCCCAATAATCMNNCACGCGGGTCGCGCAATAAT ACACC | 78 |
| 2-H3 rv4 | GGTACCCTGGCCCCAATAMNNAAACACGCGGGTCGCGCAATAAT ACACC | 79 |
| 2-H3 rv5 | GGTACCCTGGCCCCAMNNATCAAACACGCGGGTCGCGCAATAAT ACACC | 80 |
| 2-fr.3 rv | CGGTCAGGGTGGTACCCTGGC | 81 |
| Fragment 4 | | |
| 2-fr.4 fw | CGGTGTATTATTGCGCGACC | 82 |
| 2-H3 fw mix | | |
| 2-H3 fw1 | GGTGTATTATTGCGCGACCNNKGTGTTTGATTATTGGGGCCAGG GTACC | 83 |
| 2-H3 fw2 | GGTGTATTATTGCGCGACCCGCNNKTTTGATTATTGGGGCCAGG GTACC | 84 |
| 2-H3 fw3 | GGTGTATTATTGCGCGACCCGCGTGNNKGATTATTGGGGCCAGG GTACC | 85 |
| 2-H3 fw4 | GGTGTATTATTGCGCGACCCGCGTGTTTNNKTATTGGGGCCAGG GTACC | 86 |
| 2-H3 fw5 | GGTGTATTATTGCGCGACCCGCGTGTTTGATNNKTGGGGCCAGG GTACC | 87 |
| Rrt | GGAAAGCCTCTGAGGACCAGCACGGATGCCCTGTGC | 88 |
| Overlapping PCR | | |
| F1A | CGAAATTAATACGACTCACTATAGGGAGACCACAACGGTTTCCC | 89 |
| R1A | AACCCCCGCATAGGCTGGGGGTTGGAAAGCCTCTGAGGACCAGC ACG | 90 |
| PCR fragment 1 | gggagaccacaacggtttccctctagaaataattttgtttaact ttaagaaggagatatacatatggaagtgcagctgcagcagagcg gcccggaactggtgaaaccgggcgcgagcgtgaaaatgagctgc aaagcgagcggctataccttaccGATTATTATATGAAAtggt gaaacagagccatgg | 91 |

TABLE 1-continued

Sequences used in the generation of the anti-cTnT Fab fragment library

| | | |
|---|---|---|
| PCR fragment 2 | cgagcggctatacctttaccGATTATTATATGAAAtgggtgaaa cagagccatggcaaaagcctggaatggattggcGATATTAATCC GAACAACGGCGAAACCTTTtataaccagaaatttaaggataaag cgaccc | 92 |
| PCR fragment 3 | GcaaaagcctggaatggattggcGATATTAATCCGAACAACGGC GAAACCTTTtataaccagaaatttaaggataaagcgaccctgac cgtggataaaagcagcagcaccgcgtatatgcagctgaacagcc tgaccagcgaagatagcgcggtgtattattgcgcgaccCGCGTG TTTGATTATtggggccagggtaccaccctgaccg | 93 |
| PCR fragment 4 | cggtgtattattgcgcgaccCGCGTGTTTGATTATtggggccag ggtaccaccctgaccgtgagcagcgcgaaaaccaccccgccgag cgtgtatccgctg gcgccgggcagcgcggcgcagaccaacagcatggtgaccctggg ctgcctggtgaaaggctattttccggaaccggtgaccgtgacct ggaacagcggcagcctgagcagcggcgtgcatacctttccggcg gtgctgcagagcgatctgtatacctgagcagcagcgtgaccgt gccgagcagcacctggccgagcgaaaccgtgacctgcaacgtgg cgcatccggcgagcagcaccaaagtggataaaaaaattggagct ggtgcaggctctggtgctggcgcaggttctccagcagcggtgcc ggcagcagttcctgctgcggtgggcgaaggcgagggagagttca gtacgccagtttggatctcgcaggcacagggcatccgtgctggt cctcagaggctttcc | 94 |
| forward primer for cloning | GCTACAAACGCGTACGCTATGGAAGTGCAGCTGCAGCAGAGCG | 95 |

EXAMPLE 3: IN VITRO DISPLAY

The buffers for Fab display were prepared and incubated overnight at 4° C. with end-over-end rotation. Washing buffer, WB, (60 mM Tris; pH 7.5 adjusted with AcOH, 180 mM NaCl, 60 mM magnesium acetate, 5% Blocker BSA, 33 mM KCl, 200 µg t-RNA, 0.05% Tween 20); Bead wash buffer BWB (100 mM PBS, 0.1% Tween 20); Stop buffer SB (50 mM Tris pH 7.5 adjusted with AcOH, 150 mM NaCl, 50 mM magnesium acetate, 5% Blocker BSA (Pierce), 33 mM KCl, 0.5% Tween 20, 8.2 mM ox. glutathione); Elution buffer (55 mM Tris pH 7.5 adjusted with AcOH, 165 mM NaCl, 22 mM EDTA, 1 mg BSA, 5000 U rRNA (5000 U), 50 µg tRNA).

The required volume of magnetic beads (streptavidin coated beads) was blocked with 100 µL washing buffer (WB) per 10 µL initial suspension with end-over-end rotation at 4° C. overnight. 25 µL of the beads were used for the prepanning step and 20 µL for panning per target/background sample. To remove the sodium azide of the bead storage buffer, the beads were washed four times with bead washing buffer (BWB) and three times with WB. These steps were performed by applying a magnetic field for collecting the beads for two minutes and subsequently discarding the supernatant. After the final washing step the beads were resuspended in WB to their initial volume.

PUREfrex™ DS 2.0 was used according to the manufacturer's instructions, to perform in vitro transcription and translation. A 1.5 mL reaction tubes for the target (T) and one for the background (BG) were prepared.

The DNA input of expression template (LC) and display template (HC) were applied in a 2:1 molecular ratio. The amount of the DNA, coding for display and expression template were kept constant in all Fab display cycles. The in vitro transcription/translation reaction mix was incubated at 37° C. for 1 h. After incubation, the reaction was stopped by adding 100 µL stopping buffer, followed by a centrifugation step at 14 000 rpm for 15 minutes at 1° C. Unless otherwise stated, subsequent steps were performed at 4° C. The stopped supernatant of the translation mix was added to the prepared bead suspension and incubated for 30 minutes on a rocking platform. Afterwards, the suspension was centrifuged at 13 000 rpm and 1° C. for 10 minutes to separate the beads with the unspecific binding molecules from the supernatant with the remaining ternary complexes. The prepanned supernatant (300 µL) was transferred into a new 2 mL reaction tube, previously blocked with WB, and kept on ice until further use. The target (recombinant biotinylated cTnT) was added to the 300 µL prepanned supernatant in a final concentration ranging from 10 nM to 50 nM. The biotinylated cTnT concentration was decreased in every cycle in order to raise the selection pressure. The suspension was incubated for 30 minutes on a rocking platform. The solution panning step allowed the specific binding between the biotinylated cTnT and the ternary complex. Ternary complexes that bound to the target cTnT were captured with streptavidin beads in a 20 minutes incubation step. A further increase of the selection pressure was achieved in cycle III in two ways: Either by decreasing the antigen concentration to 2 nM or by using a non-biotinylated competitor. In the latter, the panning step was implemented with a low biotinylated cTnT concentration and an excess of the competitor cTnT overnight.

Washing steps comprise the capturing of the beads with the bound target-ternary complexes in a magnetic field, followed by removal of the supernatant. The beads were washed with 500 µL ice-cold WB. The selection pressure was increased in subsequent display cycles by extending the duration of the washing steps from 5 minutes to 1 hour. The final washing step was used to transfer the beads to a new blocked 2 mL reaction tube. Subsequently the beads were captured with a magnetic field and the supernatant was removed. The following elution step was performed by adding 100 µL of 1×EB containing EDTA and incubating for 10 minutes with shaking. The mRNA was released from the ternary complexes. Afterwards the elution mix was centrifuged at 14 000 rpm for 10 minutes at 1° C. The RNeasy MinElute cleanup kit (Qiagen) was used according to the manufacturer's instructions, to isolate and purify the enriched RNA. The RNA was eluted with 16 μL RNase-free water. In order to digest any remaining DNA from the selection step, the Ambion DNA-free™ kit was used according to the manufacturer's instructions. Remaining DNA cannot be amplified in subsequent PCR reactions. After DNase deactivation the suspension was centrifuged for two minutes at 13 000 rpm and at room temperature. The supernatant (50 μL) was transferred to a fresh 1.5 mL reaction tube on ice. The purified RNA was immediately used for the reverse transcription (RT). Any remaining supernatant was stored at −20° C.

The eluted mRNA was reverse transcribed to cDNA. Two reactions were set up for sample T, containing the target in the panning step. Two further reactions were prepared for sample BG and a negative control contained water. According to the number of samples a master mix was prepared and the premix was distributed to 0.2 mL reaction tubes on ice. Each reaction was inoculated with 12 μL of the eluted RNA and 0.5 μL of the reverse transcriptase. The negative control was implemented with 12 μL of RNase free water instead of RNA. The reverse transcription was performed for 45 minutes at 65° C. in a PCR thermo cycler. Subsequently the cDNA samples were incubated for 5 minutes on ice and amplified in the following steps. Remaining sample was stored at −20° C. Two PCR reactions were implemented: The first PCR "PCR on RT" was performed with the primers Frt and Rrt to amplify the cDNA of the selection pool. The second PCR "PCR on RT-PCR" using the primers F1A and R1A was applied in order to reattach the regulatory elements for the in vitro transcription/translation. Both reactions were performed with Pwo DNA polymerase.

In order to provide a sufficient DNA concentration of the selection pool, four reactions were set up for each of the samples T and BG.

Additionally, four control samples were set up. The first two samples were derived from the DNA digest after the mRNA isolation of samples T and BG and were verified by PCR to amplify potentially remaining DNA. The third and the fourth were the negative control of RT and a negative control on "PCR on RT" using PCR grade water.

The PCR product of T was purified from a preparative 1 agarose gel with the QIAquick gel extraction kit, subsequently quantified and used as a template for "PCR on RT-PCR". Three reactions of the selection pool and one negative control with PCR grade water instead of the DNA template were prepared. For each reaction, 250 ng of the previous purified "PCR on RT" were used. The PCR products were purified from a 1% preparative agarose gel with the QIAquick gel extraction Kit and were further modified for following subcloning into an appropriate expression system.

EXAMPLE 4: PERIPLASMATIC EXPRESSION OF ENRICHED BINDERS

Figure 2:
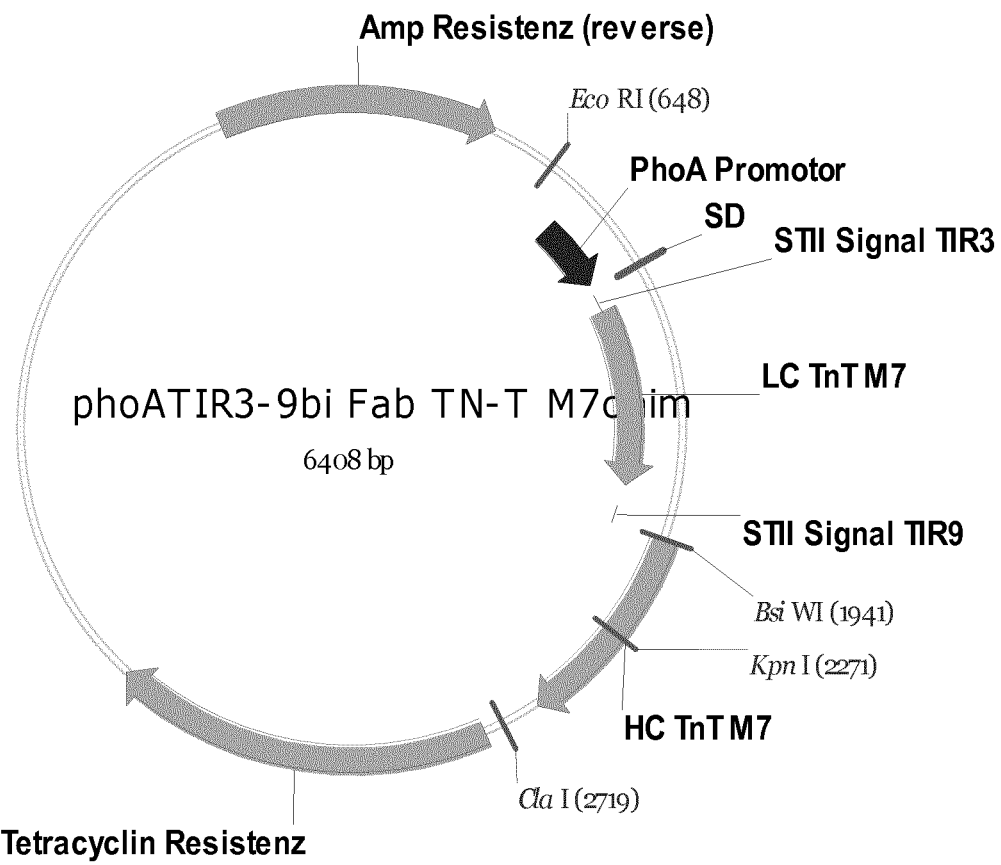
FIG. 2: Vector map for periplasmatic Fab expression
  The description in the Figure given is considered self-explaining and known to the skilled artisan.

In order to isolate enriched Fab binders, the murine variable HCs were cloned into the phoATIR3-9bi Fab TN-T M7chim expression vector (see FIG. 2), containing the human CH1 domain, murine VL domain and human CL domain of the Fab. Each selection pool was provided with a BsiWI restriction site located in the leader sequence Tir9 to enable the cloning into the expression vector.

The second restriction site KpnI occurs at the end of the variable region of the HC and thus does not have to be attached. Therefore, a PCR was performed using forward primer 5' GCTACAAACGCGTACGCTATG-GAAGTGCAGCTGCAGCAGAGCG-3' (SED ID NO: 95), containing the BsiWI restriction site and the reverse primer Rrt 5'-GGAAAGCCTCTGAGGACCAGCACG-GATGCCCTGTGC-3' (SEQ ID NO:88). Periplasmatic Expression was performed in 96-well deepwell blocks (DWBs). The preculture ("master") DWBs were filled with 1 mL LB (100 μg/mL ampicillin) per well by using the Integra VIAFlo96 and were inoculated with the isolated clones of the previously implemented subcloning and transformation. About 300 colonies per selection pool were picked. One well was left without inoculation as a negative control; another well was inoculated with an XL1 blue transformed TnT M-7 (wildtype) Fab expression vector as a positive control. The DWBs were sealed with air permeable membranes and incubated in an orbital shaker incubator (750 rpm) overnight at 30° C. Subsequently, 50 μL from each well of the master DWBs were transferred to new "expression" DWBs, prepared with 1150 mL C.R.A.P medium (100 μg/mL ampicillin) per well as described by Simmons, L. C., Reilly, D., Klimowski, L., Raju, T. S., Meng, G., Sims, P., Hong, K., Shields, R. L., Damico, L. A., Rancatore, P. & Yansura, D. G. (2002) "Expression of full-length immunoglobulins in *Escherichia coli*: rapid and efficient production of aglycosylated antibodies", J Immunol Methods 263, 133-47. The DWBs were sealed with air permeable membrane and were incubated in an orbital shaker incubator at 30° C. The induction of the Fab expression is based on the phoA promotor with the phosphate-limiting C.R.A.P medium. After 24 hours the cells with the expressed Fabs were harvested by centrifugation at 4000 rpm for 10 minutes and stored at −20° C. until further use.

The preculture master DWBs were used for "glycerol stocks" by adding 950 μL of 40% glycerol and storing at −80° C. Cell pellets were re-suspended in 50 μL B-PERII Bacterial Protein Extraction Reagent (Thermo Fisher Scientific) by vigorous vortexing of the sealed DWBs for 5 minutes and shaking for additional 10 minutes at room temperature. The cell lysates were diluted in 950 μL Tris buffer (20 mM Tris pH 7.5, 150 mM NaCl) and incubated for 10 minutes before centrifugation (10 minutes, 4000 rpm). The expression Blocks containing the crude cell extract were kept at 4° C. until further use in SPR kinetic investigations.

EXAMPLE 5: ELISA SCREEN

Figure 3:
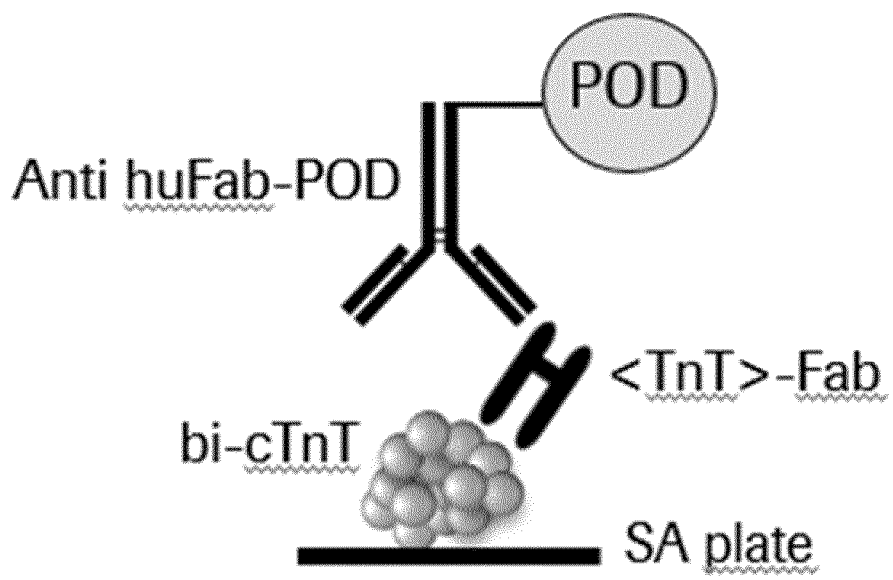
FIG. 3: ELISA setup for the screening of cTnT binding Fab fragments
  A microtiter plate coated with streptavidin (SA plate) is used to bind biotinylated cardiac troponin T (bi-cTnT) to the solid phase. Fab fragments comprising recombinant anti-cTnT heavy chains (<cTnT>-Fab) bind to TnT and are detected via peroxidase (POD)-labeled anti-human Fab antibodies (Anti huFab-POD).

To uncover the best mutant Fab binders for detailed Biacore analyses a previous Enzyme-linked Immunosorbent Assay (ELISA) was implemented. The ELISA setup is depicted in FIG. 3. Biotinylated recombinant cardiac troponin T (100 nM) was captured at a streptavidin—MTP 96 well plate for 1 h at RT by shaking on an orbital shaker. The antigen troponin T was diluted in 100 μL IP buffer (PBS pH 7.3, 1% BSA). Subsequently, the wells were washed three times with 300 μL 1× washing buffer (150 mM NaCl, 0.05% Tween20, 0.2% Bronidox) using the microplate washer BioTek ELx405 Select. After washing, the crude cell extracts containing the mutated anti-cTnT Fab binders were diluted 1:2 in IP buffer and transferred to the troponin T captured wells. Again, the wells were washed three times with 300 μL 1× washing buffer. The anti-human IgG (Fab specific)-peroxidase-labeled antibody (detection antibody) produced in goat was used at 1:40 000 dilution (in IP buffer) to detect the troponin T bound mutated Fab fragments. The wells were again washed three times with 300 μL 1× washing buffer to remove unbound detection antibody. The microplates were incubated with 100 μL ABTS per well for 30 minutes at RT. The optical density was measured with the microplate reader BioTek Power wave XS set to 405 nm. The wildtype Fab of the parent anti-cTnT antibody was used as a positive control. First hits were identified and the crude cell extract thereof were submitted to kinetic analysis.

EXAMPLE 6: SPR BASED FUNCTIONAL ANALYSES

Detailed kinetic investigations were performed at 37° C. on a GE Healthcare T200 instrument. A Biacore CM-5 series S sensor was mounted into the instrument and was preconditioned according to the manufacturer's instructions. The system buffer was HBS-ET (10 mM HEPES (pH 7.4), 150 mM NaCl, 1 mM EDTA, 0.05% (w/v) Tween® 20). The sample buffer was the system buffer supplemented with 1 mg/ml CMD (Carboxymethyldextran, Fluka). In one embodiment an anti-human antibody capture system was established on the CM5 biosensor. GAHF(ab')2, (goat anti human F(ab')2) (Code Nr.: 109-005-097, lot #13.12.2005, Jackson Immuno Research) was immobilized according to the manufacturer's instructions using NHS/EDC chemistry. 30 μg/ml GAHF(ab')2 in 10 mM sodium acetate buffer (pH 5.0) were preconcentrated to the flow cells 1, 2, 3 and 4 and were immobilized with 10.000 RU GAHF(ab')2. The sensor was subsequently saturated with 1 M ethanolamine pH 8.5.

Chimeric anti-TnT antibody fragments were periplasmatically expressed in *E. coli* cells as described and were lyzed by methods known (for technical details see: Andersen, D. C. & Reilly, D. E. (2004); Production technologies for monoclonal antibodies and their fragments. Curr Opin Biotechnol 15, 456-62). The lysates were diluted 1:20 in sample buffer. Fab fragments were captured via their humanized framework regions from the expression lysates on the biosensor at a flow rate of 10 μl/min for 1 min followed by a 2 min washing step with 10-fold concentrated HBS-EP buffer at 30 μl/min. The Fab fragment capture level (CL) in response units (RU) was monitored. Recombinant human TnT (Roche, 37 kDa) was diluted in sample buffer at 90 nM and a concentration series was produced with 0 nM, 30 nM, 11 nM, 3.3 nM, 1.1 nM, 0 nM, 3.3 nM TnT concentration. The analyte concentration series were 80 μl/min for 3 min association phase and the dissociation phase was monitored for 3 min.

At the end of the analyte association phase a report point, "binding late" (BL) in response units (RU) was monitored. After each cycle of kinetic rates determination the capture system was regenerated by a 15 seconds injection of 10 mM glycine pH 1.5 followed by two 1 min injections of 10 mM glycine pH 1.7 at 20 μl/min.

The kinetic parameters ka [1/Ms], kd [1/s], t1/2 diss [min], KD [M] and the binding stoichiometry (Molar Ratio) (for details see: Schraeml, M. & Biehl, M. (2012); Kinetic screening in the antibody development process. Methods Mol Biol 901, 171-81.) of the cTnT analyte were determined for each Fab fragment mutant with the Biaevaluation Software (GE healthcare) according to the manufacturer's instructions. Kinetic parameters were correlated to the CDR mutation sites and are listed in Table 3 according to their antigen complex stability (t1/2 diss).

Kinetic parameters were correlated to the mutations identified in the corresponding CDRs. The mutants obtained in this screening all contained more than one amino acid substitution. Mutant Fab-fragments comprising single substitutions as well as various combinations/variations of all substitution identified in the screening were then made and tested. All mutations/combinations tested are listed in Table 2.

TABLE 2

Overview over all mutants (with corresponding amino acid substitution(s)) that have been construed and analyzed

| Numbering of Mutants | CDR1 | CDR2 | CDR3 |
|---|---|---|---|
| 1 | Y34F | | |
| 2 | Y34F | F60W | |
| 3 | Y34F | F60W | V101Y |
| 4 | Y34F | F60W | Y104F |
| 5 | Y34F | F60W | V101Y + Y104F |
| 6 | Y34F | | V101Y |
| 7 | Y34F | | Y104F |
| 8 | Y34F | | V101Y + Y104F |
| 9 | Y34I | | |
| 10 | Y34I | F60W | |
| 11 | Y34I | F60W | V101Y |
| 12 | Y34I | F60W | Y104F |
| 13 | Y34I | F60W | V101Y + Y104F |
| 14 | Y34I | | V101Y |
| 15 | Y34I | | Y104F |
| 16 | Y34I | | V101Y + Y104F |
| 17 | | F60W | |
| 18 | | | V101Y |
| 19 | | | Y104F |
| 20 | | | V101Y + Y104F |
| 21 | | F60W | V101Y |
| 22 | | F60W | Y104F |
| 23 | | F60W | V101Y + Y104F |

All the above mutants have been analyzed by SPR and ranked according to their antigen complex stability (t1/2 diss), (see Table 3).

TABLE 3

Kinetic data of affinity maturated cTnT antibody Fab-fragments

| Fab CDR combinations | Capture RU | $k_a$ 1/Ms | $k_d$ 1/s | $t_{1/2}$-diss min | $K_D$ M | $R_{max}$ RU | MR | Fab CDR positions | | |
|---|---|---|---|---|---|---|---|---|---|---|
| | | | | | | | | CDR1 | CDR2 | CDR3 |
| 12 | 77 | 1.18E+06 | 3.7E−04 | 31 | 3.2E−10 | 39 | 0.5 | Y34I | F60W | Y104F |
| 5 | 76 | 2.4E+06 | 5.7E−04 | 20 | 2.3E−10 | 40 | 0.7 | Y34F | F60W | V101Y + V104F |
| 8 | 75 | 2.7E+06 | 5.2E−04 | 22 | 2.0E−10 | 41 | 0.7 | Y34F | | V101Y + Y104F |
| 4 | 71 | 2.7E+06 | 7.2E−04 | 16 | 2.7E−12 | 38 | 0.7 | Y34F | F60W | Y104F |
| 3 | 88 | 2.1E+06 | 7.9E−04 | 15 | 3.7E−10 | 49 | 0.7 | Y34F | F60W | V101Y |
| 7 | 64 | 2.4E+06 | 1.1E−03 | 11 | 4.5E−10 | 35 | 0.7 | Y34F | | Y104F |
| 2 | 101 | 2.2E+06 | 1.0E−03 | 11 | 4.6E−10 | 53 | 0.7 | Y34F | F60W | |

TABLE 3-continued

Kinetic data of affinity maturated cTnT antibody Fab-fragments

| Fab CDR combinations | Capture RU | $k_a$ 1/Ms | $k_d$ 1/s | $t_{1/2}$-diss min | $K_D$ M | $R_{max}$ RU | MR | CDR1 | CDR2 | CDR3 |
|---|---|---|---|---|---|---|---|---|---|---|
| 22 | 47 | 3.0E+06 | 1.1E−03 | 10 | 3.8E−15 | 28 | 0.7 | | F60W | Y104F |
| 19 | 49 | 2.9E+06 | 1.4E−03 | 8 | 4.6E−10 | 29 | 0.8 | | | Y104F |
| 1 | 105 | 2.3E+06 | 1.4E−03 | 8 | 6.2E−10 | 57 | 0.7 | Y34F | | |
| parental | 119 | 2.5E+06 | 1.4E−03 | 8 | 5.8E−10 | 59 | 0.6 | | | |
| 17 | 47 | 2.9E+06 | 1.6E−03 | 7 | 5.4E−10 | 27 | 0.7 | | F60W | |
| 13 | 42 | 3.0E+06 | 1.9E−03 | 6 | 6.2E−10 | 22 | 0.7 | Y34I | F60W | V101Y + Y104F |
| 9 | 74 | 2.0E+08 | 2.3E−03 | 5 | 1.2E−09 | 35 | 0.7 | Y34I | | |
| 11 | 59 | 2.2E+06 | 2.2E−03 | 5 | 1.0E−09 | 32 | 0.7 | Y34I | F60W | V101Y |
| 15 | 45 | 2.2E+06 | 2.3E−03 | 5 | 1.1E−09 | 23 | 0.7 | Y34I | | Y104F |
| 23 | 42 | 2.8E+06 | 3.4E−03 | 3 | 1.2E−09 | 20 | 0.6 | | F60W | V101Y + V104F |
| 20 | 33 | 3.1E+06 | 3.4E−03 | 3 | 1.1E−09 | 16 | 0.6 | | | V101Y + V104F |
| 21 | 42 | 2.7E+06 | 4.3E−03 | 3 | 1.6E−09 | 17 | 0.5 | | F60W | V101Y |
| 18 | 45 | 2.9E+06 | 4.7E−03 | 2 | 1.6E−09 | 19 | 0.5 | | | V101Y |
| 16 | 35 | 1.7E+06 | 5.9E−03 | 2 | 3.4E−09 | 17 | 0.6 | Y34I | | V101Y + Y104F |

Abbreviations in Table 3: ka: association rate constant [M−1s−1], kd: dissociation rate constant [s−1], KD: dissociation equilibrium constant KD [M], t/2-diss: complex half-life, ln(2)/kd*60 [min], Rmax: Response maximum of analyte [RU], MR: Molar Ratio=Ratio of Response maximum (Rmax) of analyte.

When separately analyzing the individual substitutions comprised in antibody combination 12, i.e. the mutations comprised in numbers, 9, 17 and 19 (see Table 3) it becomes clear, that there is a synergistic effect of the three mutation sites that improves the affinity, complex stability and ECL assay performance of this mutated antibody. This also demonstrates the synergistic effect of the mutations comprised therein.

EXAMPLE 7: EXPRESSION OF CHIMERIC ANTIBODIES IN HEK CELLS

Chimeric human/mouse antibodies were obtained according to standard procedures. The corresponding vector and the cloning processes are described in Norderhaug et al. J Immunol Methods. 1997 May 12; 204(1):77-87.

From several Fab fragments selected by SPR full length murine/human chimeric antibodies, i.e. antibodies with a human IgG CH1, CH2 & CH3 domains, have been constructed and produced. The cDNAs coding for the heavy and light chains were obtained from hybridoma clone 7.1 A 12.2-22 (ECACC 89060901) by RT-PCR and were cloned into separate vectors downstream of a human cytomegalovirus (CMV) immediate-early enhancer/promoter region and followed by a BGH polyadenylation signal.

The suspension-adapted human embryonic kidney FreeStyle 293-F cell line (Thermo Fisher Scientific) was used for the transient gene expression (TGE) of the antibody: The cells were transfected at approx. 2×10E6 viable cells/ml with equal amounts of the both expression plasmids (in total 0.7 mg/L cell culture) complexed by the PEIpro (Polyplus-transfection SA, Strasbourg) transfection reagent according to the manufacturer's guidelines. Three hours post-transfection, valproic acid, a HDAC inhibitor, was added (final concentration: 4 mM) in order to boost the expression. Each day, the culture was supplemented with 6% (v/v) of a soybean peptone hydrolysate-based feed. Seven days after the transfection the culture supernatant was collected by centrifugation and antibodies were purified therefrom according to standard procedures.

EXAMPLE 8: ECL MEASUREMENTS

Figure 4:
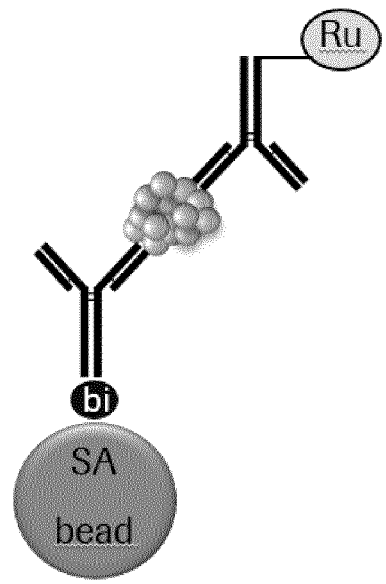
FIG. 4: Elecsys sandwich assay
  A scheme showing the assay setup is depicted. The biotinylated (bi) capture antibody is attached to streptavidin (SA) coated beads. Various affinity maturated anti-cTnT antibodies were ruthenylated (Ru) and the effect of the affinity maturations was investigated by ECL analyses.
Figure 5:
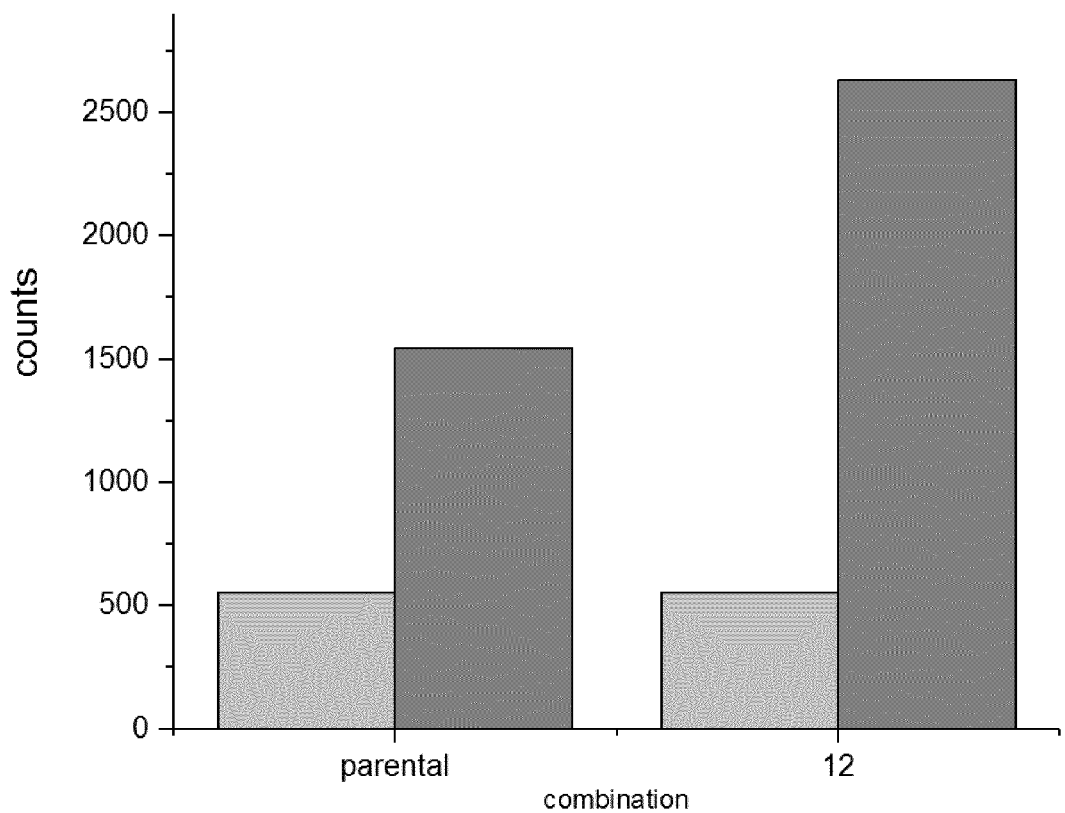
FIG. 5: ECL signal counts for the genuine specifier and a specifier derivative. Counts for the genuine anti-cTnT antibody and a mutant antibody (combination 12, respectively, refer to the Fab fragment identifier used in Table 2) are given. Light grey bars show the assay blank values (noise) in the Diluent Multi Assay reagent, dark grey bars show the counts obtained with Calibrator 1 of the commercial cTnT Elecsys® assay (signal). Antibody combination 12 shows an improved signal to noise ratio.

The antibodies produced according to Example 7 were tested in a sandwich immuno assay (see FIG. 4). IgG Ruthenium conjugates were generated and used in place of and in comparison to the original standard ruthenylated conjugate comprised in the genuine Roche Elecsys assay, catalogue number 05092744190 (Roche Diagnostics GmbH, Mannheim, Germany) in order to compare the performance of the parental anti-cTnT antibody with the mutated anti-cTnT antibodies. The mutated mAbs were conjugated to ruthenium at different labeling stoichiometries. In one embodiment the ruthenium labeling molar ratio was 1:10 antibody IgG:label. The ruthenium conjugates from anti-cTnT antibody variants were diluted in the Elecsys R2 reagent and measurements performed on a Cobas E170 Module using the Troponin T hs assay protocol with a blank control (Diluent Universal, Id. 11732277122, Diluent Multi Assay, Id. 03609987170, Roche Diagnostics GmbH, Mannheim, Germany), Cal1 and Cal2 from Troponin T hs CalSet (Id. 05092752190, Roche Diagnostics GmbH, Mannheim, Germany) using the Troponin T hs assay specifications. Results are given in FIG. 5. Antibodies comprising the mutations present in combinations number 11 and 12, respectively, show an improved signal to noise ratio as compared to the parent (non-mutated) antibody.

The invention claimed is:

1. An antibody that specifically binds to human cardiac troponin T (SEQ ID NO:1) being characterized in that the CDRs comprise in the light chain variable domain a CDR1 comprising the amino acid sequence of SEQ ID NO:2, a CDR2 comprising the amino acid sequence of SEQ ID NO:3, and a CDR3 comprising the amino acid sequence of SEQ ID NO:4, and in the heavy chain variable domain one of the following:
   (i) a CDR1 comprising the amino acid sequence of SEQ ID NO:6, a CDR2 comprising the amino acid sequence of SEQ ID NO:9, and a CDR3 comprising the amino acid sequence of SEQ ID NO: 12,
   (ii) a CDR1 comprising the amino acid sequence of SEQ ID NO:7, a CDR2 comprising the amino acid sequence of SEQ ID NO:8, and a CDR3 comprising the amino acid sequence of SEQ ID NO: 11,
   (iii) a CDR1 comprising the amino acid sequence of SEQ ID NO:7, a CDR2 comprising the amino acid sequence of SEQ ID NO:8, and a CDR3 comprising the amino acid sequence of SEQ ID NO: 13,
   (iv) a CDR1 comprising the amino acid sequence of SEQ ID NO:7, a CDR2 comprising the amino acid sequence of SEQ ID NO:9, and a CDR3 comprising the amino acid sequence of SEQ ID NO: 13,
   (v) a CDR1 comprising the amino acid sequence of SEQ ID NO:6, a CDR2 comprising the amino acid sequence of SEQ ID NO:9, and a CDR3 comprising the amino acid sequence of SEQ ID NO: 10,
   (vi) a CDR1 comprising the amino acid sequence of SEQ ID NO:7, a CDR2 comprising the amino acid sequence of SEQ ID NO:9, and a CDR3 comprising the amino acid sequence of SEQ ID NO: 11,
   (vii) a CDR1 comprising the amino acid sequence of SEQ ID NO:7, a CDR2 comprising the amino acid sequence of SEQ ID NO:9, and a CDR3 comprising the amino acid sequence of SEQ ID NO: 12,
   (viii) a CDR1 comprising the amino acid sequence of SEQ ID NO:7, a CDR2 comprising the amino acid sequence of SEQ ID NO:9, and a CDR3 comprising the amino acid sequence of SEQ ID NO: 10,
   (ix) a CDR1 comprising the amino acid sequence of SEQ ID NO:7, a CDR2 comprising the amino acid sequence of SEQ ID NO:8, and a CDR3 comprising the amino acid sequence of SEQ ID NO: 12, or
   (x) a CDR1 comprising the amino acid sequence of SEQ ID NO:5, a CDR2 comprising the amino acid sequence of SEQ ID NO:9, and a CDR3 comprising the amino acid sequence of SEQ ID NO: 12.

2. An antibody according to claim 1, wherein the antibody has a t/2-diss at 37° C. of 10 minutes or longer.

3. A composition comprising the antibody of claim 1.

4. An antibody comprising:
a light chain variable domain consisting of framework regions (FW) and CDRs as represented in formula I:

FW(LC)1-CDR(LC)1-FW(LC)2-CDR(LC)2-FW(LC)
3-CDR(LC)3-FW(LC)4         (formula I)

and a heavy chain variable domain consisting of FWs and CDRs as represented in formula II:

FW(HC)1-CDR(HC)1-FW(HC)2-CDR(HC)2-FW
(HC)3-CDR(HC)3-FW(HC)4         (formula II), wherein the FWs comprise the following amino acid sequences or a variant thereof that is at least 85% identical thereto and wherein the CDRs comprise the sequences as defined in claim 1:
in the light chain
FW(LC)1 the amino acid sequence of SEQ ID NO: 14;
FW(LC)2 the amino acid sequence of SEQ ID NO: 15;
FW(LC)3 the amino acid sequence of SEQ ID NO: 16;
FW(LC)4 the amino acid sequence of SEQ ID NO: 17;
and in the heavy chain
FW(HC)1 the amino acid sequence of SEQ ID NO:18;
FW(HC)2 the amino acid sequence of SEQ ID NO: 19;
FW(HC)3 the amino acid sequence of SEQ ID NO:20;
FW(HC)4 the amino acid sequence of SEQ ID NO:21.

5. An antibody comprising:
   (i) a light chain variable domain comprising the amino acid sequence of SEQ ID NO:22, and
   (ii) a heavy chain variable domain comprising an amino acid sequence selected from the amino acid sequences of SEQ ID NO:23; SEQ ID NO:24; SEQ ID NO:25; SEQ ID NO:26; SEQ ID NO: 27; SEQ ID NO:28; SEQ ID NO:29; SEQ ID NO:30; SEQ ID NO:31; and SEQ ID NO: 32.

6. The antibody of claim 5, wherein the antibody specifically binds to human cardiac troponin T and has a t/2-diss at 37° C. of 10 minutes or longer.

7. An antibody comprising:
   (i) a light chain variable domain consisting of the amino acid sequence of SEQ ID NO: 22, and
   (ii) a heavy chain variable domain consisting of the amino acid sequence selected from the amino acid sequences of SEQ ID NO:23; SEQ ID NO:24; SEQ ID NO:25; SEQ ID NO:26; SEQ ID NO: 27; SEQ ID NO:28; SEQ ID NO:29; SEQ ID NO:30; SEQ ID NO:31; and SEQ ID NO:32,
wherein the CDRs are as defined in claim 1.

8. The antibody of claim 7, wherein the antibody specifically binds to human cardiac troponin T and has a t/2-diss at 37° C. of 10 minutes or longer.

9. A composition comprising the antibody of claim 7.

10. An antibody comprising:
(i) a light chain variable domain consisting of the amino acid sequence of SEQ ID NO: 22, and
(ii) a heavy chain variable domain consisting of an amino acid sequence selected from the amino acid sequences of SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; and SEQ ID NO: 32.

* * * * *